US011639506B2

(12) United States Patent
Piotrowski et al.

(10) Patent No.: US 11,639,506 B2
(45) Date of Patent: May 2, 2023

(54) RECOMBINANT YEAST HAVING INCREASED TOLERANCE TO IONIC LIQUIDS AND METHODS OF USE

(71) Applicant: Wisconsin Alumni Research Foundation, Madison, WI (US)

(72) Inventors: Jeff Scott Piotrowski, Madison, WI (US); Scott Bottoms, Madison, WI (US); Quinn Dickinson, Madison, WI (US); Robert Chase Landick, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/154,537

(22) Filed: May 13, 2016

(65) Prior Publication Data

US 2016/0333362 A1 Nov. 17, 2016

Related U.S. Application Data

(60) Provisional application No. 62/162,043, filed on May 15, 2015.

(51) Int. Cl.
| | | |
|---|---|---|
| C12N 15/81 | (2006.01) | |
| C12P 7/10 | (2006.01) | |
| C12P 19/02 | (2006.01) | |

(52) U.S. Cl.
CPC ............... *C12N 15/81* (2013.01); *C12P 7/10* (2013.01); *C12P 19/02* (2013.01); *Y02E 50/10* (2013.01)

(58) Field of Classification Search
None
See application file for complete search history.

(56) References Cited

U.S. PATENT DOCUMENTS

2013/0295620 A1* 11/2013 Albers .................. C12P 7/10
435/99

OTHER PUBLICATIONS

Walker et al. (BMC Genomics, vol. 15, pp Article No. 552, Jul. 3, 2014) (Year: 2014).*
Abadjieva, A., et al., 2001, "A new yeast metabolon involving at least the two first enzymes of arginine biosynthesis: acetylglutamate synthase activity requires complex formation with acetylglutamate kinase", J. Biol. Chem. 276, 42869-42880.
Almeida et al., "Stress-related challenges in pentose fermentation to ethanol by the yeast *Saccharomyces cerevisiae*". Biotech. J. 6:286 (2011).
Almeida, J.R., et al., 2007, "Increased tolerance and conversion of inhibitors in lignocellulosic hydrolysates by *Saccharomyces cerevisiae*", J. Chem. Technol. Biotechnol. 82, 340-349.

Bond et al., "Integrated Catalytic Conversion of γ-Valerolactone to Liquid Alkenes for Transportation Fuels", Science 26: (2010).
Dickinson, et al., "Mechanism of Imidazolium Ionic Liquids Toxicity in *Saccharomyces cerevisiae* and Rational Engineering of a Tolerant, Xylose-Fermenting Strain"; Microb Cell Fact (2016) 15:17 (including supplementary materials and methods).
Docherty, K.M., et al., 2005, "Toxicity and antimicrobial activity of imidazolium and pyridinium ionic liquids", Green Chem. 7, 185-189. doi:10.1039/B419172B.
Eraso, P., et al., 2006, "Yeast protein kinase Ptk2 localizes at the plasma membrane and phosphorylates in vitro the C-terminal peptide of the H+-ATPase", Biochim. Biophys. Acta BBA—Biomembr. 1758, 164-170. doi:10.1016/j.bbamem.2006.01.010.
Erez & Kahana, "Screening for Modulators of Spermine Tolerance Identifies Sky1, the SR Protein Kinase of *Saccharomyces cerevisiae*, as a Regulator of Polyamine Transport and Ion Homeostasis," Mol. Cell. Biol. 21:175-184 (2001).
Erez, & Kahana, 2002, "Deletions of SKY1 or PTK2 in the *Saccharomyces cerevisiae* trk1 Dellalik2Delta mutant cells exert dual effect on ion homeostasis", Biochem. Biophys. Res. Commun. 295, 1142-1149.
Fung, S.-Y., et al., 2013, "Unbiased screening of marine sponge extracts for anti-inflammatory agents combined with chemical genomics identifies girolline as an inhibitor of protein synthesis," ACS Chem. Biol. 9.1 (2013): 247-257.
Goossens et al., "Regulation of Yeast H+-ATPase by Protein Kinases Belonging to a Family Dedicated to Activation of Plasma Membrane Transporters," Mol. Cell. Biol. 20:7654-7661 (2000).
Kaouass et al., 1997, "The STK2 gene, which encodes a putative Ser/Thr protein kinase, is required for high-affinity spermidine transport in *Saccharomyces cerevisiae*"; Mol. Cell. Biol. 17, 2994-3004.
Keating, D.H., et al., 2014. "Aromatic inhibitors derived from ammonia-pretreated lignocellulose hinder bacterial ethanologenesis by activating regulatory ciicuits controlling inhibitor efflux and detoxification"; Microb. Physiol. Metab. 5, 402. doi:10.3389/fmicb.2014.00402.
Kucharczyk, et al., 2000. "The novel protein Ccz1p required for vacuolar assembly in *Saccharomyces cerevisiae* functions in the same transport pathway as Ypt7", p. J. Cell Sci. 113 Pt 23, 4301-4311.
Laluce, C., et al. "Pombeiro-Sponchiado 448 SR. 2012. Advances and Developments in Strategies to Improve Strains of 449 *Saccharomyces cerevisiae* and Processes to Obtain the Lignocellulosic Ethanol—A 450 Review." Appl. Biochem. Biotechnol 166: 1908-1926.
Lee, C.M., et al., 1999. "The DNA helicase, Hmi1p, is transported into mitochondria by a C-terminal cleavable targeting signal." J. Biol. Chem. 274, 20937-20942.

(Continued)

*Primary Examiner* — Richard G Hutson
(74) *Attorney, Agent, or Firm* — Schwegman Lundberg & Woessner, P.A.

(57) ABSTRACT

The present invention relates to materials and methods for the production of ethanol. More particularly, the present invention provides genetically modified strains of *Saccharomyces cerevisiae* having enhanced tolerance for ionic liquid (IL) toxicity. Also provided are methods of using such genetically engineered yeast strains for improved IL-mediated hydrolysis of lignocellulosic biomass for industrial-scale production of various fuels, chemical feedstocks, and synthetic polymers.

17 Claims, 7 Drawing Sheets

Specification includes a Sequence Listing.

(56) References Cited

OTHER PUBLICATIONS

Li, et al., 1998. "Glucose repression on RIM1, a gene encoding a mitochondrial single-stranded DNA-binding protein, in *Saccharomyces cerevisiae*: a possible regulation at pre-mRNA splicing." Curr. Genet. 34, 351-359.

Li, C., et al., 2013. "Scale-up and evaluation of high solid ionic liquid pretreatment and enzymatic hydrolysis of switchgrass," Biotechnol. Biofuels 6, 1-14. doi:10.1186/1754-6834-6-154.

Liu, "Molecular mechanisms of yeast tolerance and in situ detoxification of lignocellulose hydrolysates", Applied Microbiol. Biotech. 90:809 (2011).

Luterbacher et al., "Nonenzymatic Sugar Production from Biomass Using Biomass-Derived γ-Valerolactone"; Science 343:277-280 (2014).

Lynd et al., "Microbial Cellulose Utilization: Fundamentals and Biotechnology", Microbiol. Mol. Biol. Rev. 66:506-577 (2002).

Mortimer and Johnston, "Genealogy of Principal Strains of the Yeast Genetic Stock Center," Genetics 113 (1):35-43 (1986).

Ni et al., "Transposon Mutagenesis to Improve the Growth of Recombinant *Saccharomyces cerevisiae* on D-Xylose", Applied Environmental Microbiol. 73:2061 (2007).

Ouellet et al., "Impact of ionic liquid pretreated plant biomass on *Saccharomyces cerevisiae* growth and biofuel production"; Green Chemistry 13:2743-2749 (2011).

Palmqvist and Hahn-Hägerdal, 2000. "Fermentation of lignocellulosic hydrolysates. II: inhibitors and mechanisms of inhibition"; Bioresour. Technol. 74, 25-33. doi:10.1016/S0960-8524(99)00161-3.

Parreiras, et al., 2014, "Engineering and Two-Stage Evolution of a Lignocellulosic Hydrolysate-Tolerant *Saccharomyces cerevisiae* Strain for Anaerobic Fermentation of Xylose from AFEX Pretreated Corn Stove," PLoS ONE 9, e107499. doi:10.1371/journal.pone.0107499.

Parsons, A., 2006. "Exploring the mode-of-action of bioactive compounds by chemical-genetic profiling in yeast"; Cell 126, 611-625.

Piotrowski, J.S., et al., 2014. "Death by a thousand cuts: the challenges and diverse landscape of lignocellulosic hydrolysate inhibitors"; Frontiers in Microbiology, Mar. 2014, vol. 5, Article 90, 8 pages.

Sato, T.K., et al., 2013. "Harnessing genetic diversity in *Saccharomyces cerevisiae* for improved fermentation of xylose in hydrolysates of alkaline hydrogen peroxide pretreated biomass"; Appl. Environ. Microbiol, Jan. 2014, vol. 30, No. 2 540-554, AEM.01885-13. doi:10.1128/AEM.01885-13.

Schneider et al., 1997. "Two genes of the putative mitochondrial fatty acid synthase in the genome of *Saccharomyces cerevisiae*"; Curr. Genet. 32, 384-388.

Socha, A.M., et al., 2014. "Efficient biomass pretreatment using ionic liquids derived from lignin and hemicellulose"; Proc. Natl. Acad. Sci. 111, E3587-E3595.

Taylor et al., "Understanding physiological responses to pretreatment inhibitors in ethanologenic fermentations", Biotechnology J. 7:1169 (2012).

Walfridsson et al., "Xylose-metabolizing *Saccharomyces cerevisiae* strains overexpressing the TKL1 and TAL1 genes encoding the pentose phosphate pathway enzymes transketolase and transaldolase", Applied Environmental Microbiol. 61:4184 (1995).

Engineering and Two-Stage Evolution of a Lignocellulosic Hydrolysate-Tolerant *Saccharomyces cerevisiae* Strain for Anaerobic Fermentation of Xylose from AFEX Pretreated Corn Stover, Lucas S. Parreiras . . . , Sep. 2014, vol. 9, Issue 9, e107499.

* cited by examiner

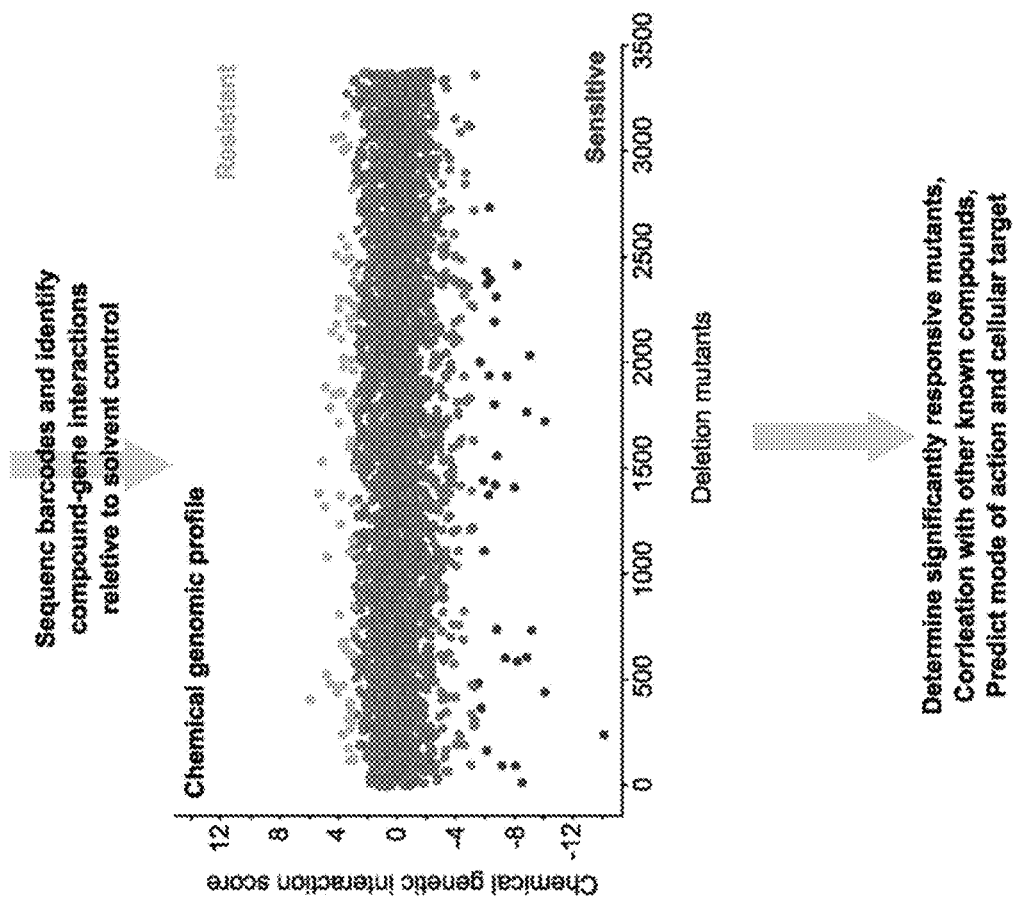

FIGS. 2A-C
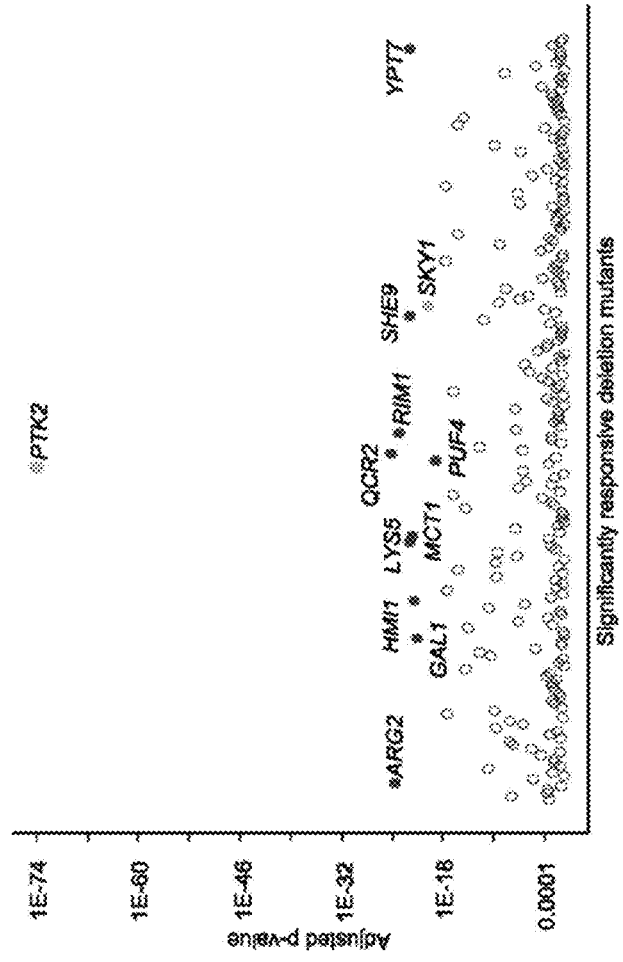
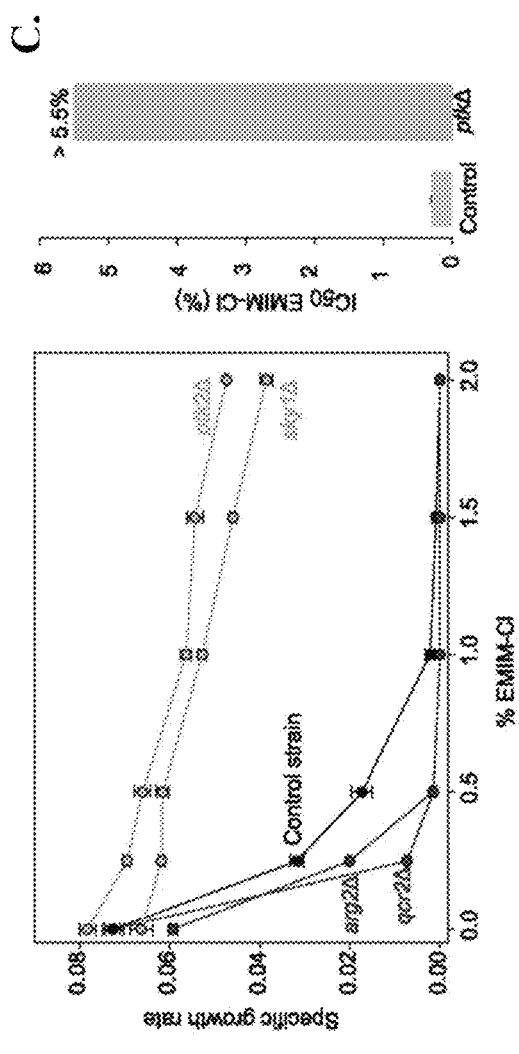

```
                            SEQUENCE LISTING

<160> NUMBER OF SEQ ID NOS: 2

<210> SEQ ID NO 1
<211> LENGTH: 818
<212> TYPE: PRT
<213> ORGANISM: Saccharomyces cerevisiae

<400> SEQUENCE: 1

Met Ala Gly Asn Gly Lys Asp Lys Glu Val Asp Lys Ser Pro Ser Val
1               5                   10                  15

Ser Thr Leu Lys Leu Leu Gly Lys Arg Leu Phe Asn Ser Ser Ser His
            20                  25                  30

Thr Asp Asn Ser Ser Leu Leu Leu Ser Ala Glu Gln Leu Gly Asn Gly
        35                  40                  45

Arg Ser Leu Arg Lys Arg Pro Thr Ser Pro Ser Ile Ser Gly Ser Gly
    50                  55                  60

Ser Gly Gly Asn Ser Pro Ser Ser Ser Ala Gly Ala Arg Gln Arg Ser
65                  70                  75                  80

Ala Ser Leu His Arg Arg Lys Asn Asn Ala Ser Val Gly Phe Ser Asn
                85                  90                  95

Gly Ser Val Ser Ser His Lys Ser Ser Val Ala Leu Gln Asp Leu Ile
            100                 105                 110

Lys His Asn Asn Asn Pro Tyr Leu Asn Ser Pro Ser Asp Ile Leu Gly
        115                 120                 125

Thr Gly Thr Gly Ile Ala Ser Thr Arg Asp Arg Asp Arg Ala Val Leu
    130                 135                 140

Asp Arg Glu Lys Glu Lys Glu Arg Ala Arg Asn Lys Glu Arg Asn Thr
145                 150                 155                 160

His His Ala Gly Leu Pro Gln Arg Ser Asn Ser Met Ala Ser His His
                165                 170                 175

Phe Pro Asn Glu Asn Ile Val Tyr Asn Pro Tyr Gly Ile Ser Pro Asn
            180                 185                 190

His Ala Arg Pro Asp Thr Ala Phe Ala Asp Thr Leu Asn Thr Asn Lys
        195                 200                 205

Glu Asn Asp Leu Ser Phe Tyr Met His Asp Gly Asn Ser Lys Ile Arg
    210                 215                 220

Met Leu Pro Leu Pro Ile Ala Asn Pro Asn Asp Phe Leu Pro Glu Asp
225                 230                 235                 240

Met Lys Gln Tyr Ser Val His Leu Thr Asp Asn Phe Val Phe Asp Thr
                245                 250                 255

Asp Asn Lys Pro Ile Gly Ser Gly Gly Ser Ser Glu Val Arg Lys Val
            260                 265                 270

Lys Ser Ser Tyr Arg Gln Lys Asp Val Tyr Ala Leu Lys Lys Leu Asn
        275                 280                 285

Met Ile Tyr His Glu Ser Pro Glu Lys Tyr Lys Arg Cys Ser Lys
    290                 295                 300

Glu Phe Ile Ile Ala Lys His Leu Ser His Asn Val His Ile Thr Asn
305                 310                 315                 320

Thr Phe Tyr Leu Leu Lys Val Pro Thr Thr Tyr Thr Thr Arg Gly
                325                 330                 335
```

```
Trp Gly Phe Ile Met Glu Leu Gly Val Lys Asp Leu Phe Gln Leu Met
            340                 345                 350

Glu Arg Thr Gly Trp Lys Asn Val Pro Phe Asn Glu Lys Tyr Cys Leu
        355                 360                 365

Phe Lys Gln Val Ala Gln Gly Ile Lys Phe Cys His Asp Asn Gly Ile
    370                 375                 380

Ala His Arg Asp Leu Lys Pro Glu Asn Val Leu Ile Ser Lys Glu Gly
385                 390                 395                 400

Ile Cys Lys Leu Thr Asp Phe Gly Ile Ser Asp Trp Tyr His Val Ile
                405                 410                 415

Pro His Asp Tyr Thr Ser Pro Val Lys Thr Cys Gln Gly Met Ile Gly
            420                 425                 430

Ser Pro Pro Tyr Thr Pro Pro Glu Val Met Tyr Phe Asp Ala Lys Lys
        435                 440                 445

His Tyr Pro Glu Lys Phe Gln Lys Pro Tyr Asn Pro Leu Ala Met Asp
    450                 455                 460

Ser Tyr Ala Leu Gly Ile Met Leu Ile Thr Met Ile Asn Asn Ile Ile
465                 470                 475                 480

Pro Phe Ile Asp Ser Cys Asn Thr Asp Ala Arg Phe Arg Glu Phe Glu
                485                 490                 495

Val Ser Tyr Asp Asn Phe Ile Asn His Gln Asn Pro His Phe Arg Asp
            500                 505                 510

Lys Gly Cys His Lys Pro Gly Pro Gly Ser Glu Tyr Ser Leu Ala Arg
        515                 520                 525

Asn Phe Lys Asn Thr Asp Ala Thr Arg Ile Ala Trp Arg Leu Ala Asp
    530                 535                 540

Pro Asn Pro Ala Thr Arg Tyr Thr Met Asp Asp Leu Phe Asn Asp Pro
545                 550                 555                 560

Phe Phe Gln Gln Ile Glu Thr Cys Val Glu Pro Asn Asp Asp Leu
                565                 570                 575

Val Arg Val Pro Glu Leu Arg Lys Ser Thr Ser Thr Asn Asp Phe Ser
            580                 585                 590

Glu Asn Ser Leu Asp Ala Pro His Asp Gln Glu Val Ile His Thr Ser
        595                 600                 605

Asn Pro Phe Leu Lys Lys Glu Thr Leu Thr Ser Lys Pro Arg Ser Met
    610                 615                 620

Leu Glu Ile Ala Glu Ser Pro Ser Leu Lys Gln Lys Ser Lys Val Lys
625                 630                 635                 640

Asp Ser Ala Lys Thr Lys Thr His Asp Val Gly Asp Glu Gly Gly Asn
                645                 650                 655

Glu Ser Thr Lys Pro Lys Gln Gln Asp Lys Lys Glu Asn Leu Lys Lys
            660                 665                 670

Asp Glu Val Lys Asn Gly Asp Lys Asp Lys Val Ile Glu Glu Ala Thr
        675                 680                 685

Thr Thr Asn Val Asp Ser Ile Leu Glu Lys Pro Thr Pro Thr Ser Thr
    690                 695                 700

Lys Val Glu Asp Asn Leu Ser Glu Asp Ser Thr Met Lys Glu Leu
705                 710                 715                 720

Lys Ser Met Leu Asn Ser Thr Pro Thr Pro Thr His Asn Gly Pro
                725                 730                 735

Thr Pro Leu Pro Ala Lys Ala Gly Thr Gln Leu Asp Lys Arg Met Ser
            740                 745                 750
```

```
Asp Leu Ser Leu Lys Ser Glu Thr Pro Ala Ser Thr Lys Asn Phe Ser
        755                 760                 765

Ala Pro Asn Val Ser Ser Ser Asn Ser Leu Arg Ser Leu Gly Ser
770                 775                 780

Pro Ser Val Ser Ser Lys Lys Lys Val Ile His His His Leu
785                 790                 795                 800

Asp Ile Thr Asn Ser Val Thr Asn Met Ser Ser Val Ser Ala Phe Ile
                    805                 810                 815

Ser Arg

<210> SEQ ID NO 2
<211> LENGTH: 742
<212> TYPE: PRT
<213> ORGANISM: Saccharomyces cerevisiae

<400> SEQUENCE: 2

Met Gly Ser Ser Ile Asn Tyr Pro Gly Phe Val Thr Lys Ser Ala His
1               5                   10                  15

Leu Ala Asp Thr Ser Thr Asp Ala Ser Ile Ser Cys Glu Glu Ala Thr
                20                  25                  30

Ser Ser Gln Glu Ala Lys Lys Asn Phe Phe Gln Arg Asp Tyr Asn Met
            35                  40                  45

Met Lys Lys Ala Pro Ala Pro Thr Lys Ser Lys Leu Ser Leu Ala Leu
    50                  55                  60

Gln Thr Ser Lys Ser Ser Ser Ala Asn Gly Thr Val Gln Glu Asp
65              70                  75                  80

Thr Ser Ser Lys Thr Glu Asp Phe Ser Thr Lys Ser Ile Lys Lys Lys
                85                  90                  95

Pro Asp Ser Gly Val Glu Ser His Val Ser Ile Gln Ser Asp Ser Gly
            100                 105                 110

Pro Gln Ser Asp Ser Asp Leu Asp Ser Asp Ser Ser Ile Ser Ser Cys
        115                 120                 125

Asp Glu Arg Asn Glu Glu Ser Leu Lys Asp Tyr Arg Pro Gly Gly Tyr
    130                 135                 140

His Pro Ala Phe Lys Gly Glu Pro Tyr Lys Asp Ala Arg Tyr Ile Leu
145                 150                 155                 160

Val Arg Lys Leu Gly Trp Gly His Phe Ser Thr Val Trp Leu Ala Lys
                165                 170                 175

Asp Met Val Asn Asn Thr His Val Ala Met Lys Ile Val Arg Gly Asp
            180                 185                 190

Lys Val Tyr Thr Glu Ala Ala Glu Asp Glu Ile Lys Leu Leu Gln Arg
        195                 200                 205

Val Asn Asp Ala Asp Asn Thr Lys Glu Asp Ser Met Gly Ala Asn His
    210                 215                 220

Ile Leu Lys Leu Leu Asp His Phe Asn His Lys Gly Pro Asn Gly Val
225                 230                 235                 240

His Val Val Met Val Phe Glu Val Leu Gly Glu Asn Leu Leu Ala Leu
                245                 250                 255

Ile Lys Lys Tyr Glu His Arg Gly Ile Pro Leu Ile Tyr Val Lys Gln
            260                 265                 270

Ile Ser Lys Gln Leu Leu Leu Gly Leu Asp Tyr Met His Arg Arg Cys
        275                 280                 285

Gly Ile Ile His Thr Asp Ile Lys Pro Glu Asn Val Leu Met Glu Ile
    290                 295                 300
```

```
Gly Asp Val Glu Gly Ile Val Gln Met Val Glu Ala Leu Asp Lys Gln
305                 310                 315                 320

Lys Arg Glu Ala Lys Arg Leu Gln Arg His Val Ser Arg Ser Ser Asp
            325                 330                 335

Ile Thr Ala Asn Asp Ser Ser Asp Glu Lys Trp Ala Glu Cys Gln Thr
                340                 345                 350

Ser Met Pro Cys Gly Ser Ser Asn Ser Lys Ser Arg Ser Ile Glu
            355                 360                 365

Lys Asp Leu Ser Lys Arg Cys Phe Arg Arg Pro Arg His Thr Ile
370                 375                 380

Ile Thr Gly Ser Gln Pro Leu Pro Ser Pro Ile Ser Ser Ser Asn Phe
385                 390                 395                 400

Phe Glu Met Arg Ala His Phe Cys Gly Ser Ser His Asn Ser Phe Ser
                405                 410                 415

Ser Val Ser Gly Asn Arg Asn Ile Pro Ser Ser Ile Asn Asn Asn Ser
            420                 425                 430

Ile Asn Asn Gly Ile Gly Ile Lys Asn Ser Asn Asn Ser Phe Leu Asn
                435                 440                 445

Ser Val Pro His Ser Val Thr Arg Met Phe Ile Asn Glu Asp Ser Asn
            450                 455                 460

Asp Asn Asn Asn Asn Asp Asn Ser Lys Asn Lys Asn Asn Asn Asn
465                 470                 475                 480

Asn Ser Asn Asn Asn Asn Asn Glu Asp Ile Met Asn Thr Pro Leu His
                485                 490                 495

Glu Glu Gln Leu Ala Asp Ser Leu Ser Thr Phe Asp Ile Ser Asn Ile
            500                 505                 510

Ser Gln Ser Ser Asp Thr Asn Gly Pro Tyr Ile Ser Asn Thr Met Asp
            515                 520                 525

Ser Asn Ser Asn Val Ser Thr Asp Ile Asn Ser Pro Glu Asn Leu Ile
530                 535                 540

Gln Ile Lys Ile Ala Asp Leu Gly Asn Ala Cys Trp Tyr Asp Glu His
545                 550                 555                 560

Tyr Thr Asn Ser Ile Gln Thr Arg Glu Tyr Arg Ser Pro Glu Val Leu
                565                 570                 575

Leu Gly Ala Pro Trp Gly Cys Gly Ala Asp Ile Trp Ser Thr Ala Cys
            580                 585                 590

Leu Ile Phe Glu Leu Ile Thr Gly Asp Phe Leu Phe Glu Pro Asp Glu
                595                 600                 605

Gly His Ser Tyr Thr Lys Asp Asp His Ile Ala Gln Ile Ile Glu
            610                 615                 620

Leu Leu Gly Glu Leu Pro Ser Tyr Leu Leu Arg Asn Gly Lys Tyr Thr
625                 630                 635                 640

Arg Thr Phe Phe Asn Ser Arg Gly Leu Leu Arg Asn Ile Ser Lys Leu
                645                 650                 655

Lys Phe Trp Pro Leu Glu Asp Val Leu Thr Glu Lys Tyr Lys Phe Ser
            660                 665                 670

Lys Asp Glu Ala Lys Glu Ile Ser Asp Phe Leu Ser Pro Met Leu Gln
            675                 680                 685

Leu Asp Pro Arg Lys Arg Ala Asp Ala Gly Gly Leu Val Asn His Pro
690                 695                 700

Trp Leu Lys Asp Thr Leu Gly Met Glu Glu Ile Arg Val Pro Asp Arg
705                 710                 715                 720
```

```
Glu Leu Tyr Gly Ser Gly Ser Asp Ile Pro Gly Trp Phe Glu Glu Val
                725             730             735
Arg Asp His Lys Arg His
            740
```

RECOMBINANT YEAST HAVING INCREASED TOLERANCE TO IONIC LIQUIDS AND METHODS OF USE

CROSS-REFERENCE TO RELATED APPLICATIONS

The present non-provisional application claims the benefit of U.S. Provisional Application 62/162,043, filed May 15, 2015, which is incorporated by reference herein its entirety for all purposes.

STATEMENT REGARDING FEDERALLY SPONSORED RESEARCH OR DEVELOPMENT

This invention was made with government support under DE-FC02-07ER64494 awarded by the US Department of Energy. The government has certain rights in the invention.

FIELD OF THE INVENTION

Broadly, the present invention relates to materials and methods for the production of biofuels and other industrially relevant products from plant materials such as chemical feedstocks. In particular, the present invention relates to genetically modified yeast strains useful for glucose and xylose fermentation and, more specifically, to strains of *Saccharomyces cerevisiae* genetically engineered for enhanced tolerance to ionic liquid toxicity and methods of using the same for improved ionic liquid-mediated hydrolysis of lignocellulosic biomass for industrial-scale ethanol production.

BACKGROUND

Cellulosic biomass is a vast source of renewable energy and an abundant substrate for biofuel production. As an alternative to corn-based ethanol, bioethanol can be generated from lignocellulosic (LC) sugars derived from cellulosic biomass of renewable and sustainable plant feedstocks. Energy of cellulosic biomass is primarily stored as the recalcitrant polysaccharide cellulose, which is difficult to hydrolyze because of the highly crystalline structure, and in hemicellulose, which presents challenges because of its structural diversity and complexity. Many microbes cannot natively ferment pentose sugars (e.g., xylose) from complex lignocellulosic biomass, which is composed of cellulose, hemicellulose and lignin fractions. Even when engineered to express the minimal enzymes from native pentose sugar-metabolizing organisms, *S. cerevisiae* cannot ferment xylose from innocuous lab media at industrially-acceptable rates. Laluce et al., *Applied Microbiol. Biotech.* 166:1908 (2012); Almeida et al., *Biotech. J.* 6:286 (2011). Xylose is a prevalent sugar in both woody and herbaceous plants and a major component of hemicelluloses. Bioconversion of both xylose and glucose is required for the production of cellulosic biofuels. To further complicate matters, plant biomass must be chemically, mechanically, or thermally pretreated prior to enzymatic hydrolysis ex situ in order to produce fermentable glucose and xylose monomers. Such pretreatment processes generate a diverse array of degradation products derived from plant cell walls, such as hemicellulose and lignin-derived acetate and aromatic molecules, many of which inhibit cellular metabolism in *S. cerevisiae* and induce microbial stress during hydrolysate fermentation. Taylor et al., *Biotechnology J.* 7:1169 (2012); Liu, *Applied Microbiol. Biotech.* 90:809 (2011). At present, little is known about how such inhibitors impact xylose fermentation, particularly under strict industrially relevant, anaerobic conditions where ethanol production is maximized.

In view of the current state of the biofuel industry, particularly ethanol production based on glucose- and xylose-containing feedstocks, it can be appreciated that there remains a need for efficient and cost-effective processes for breaking down cellulose and hemicellulose into their constituent sugars.

SUMMARY OF THE INVENTION

The present invention is largely related the inventors' research efforts to better understand xylose utilization for microbial engineering. The invention relates generally to methods and compositions for digesting lignocellulosic material and more particularly to methods that involve exposing the material to genetically engineered *Saccharomyces cerevisiae* (*S. cerevisiae*) variants having enhanced tolerance for or resistance to ionic liquid-mediated toxicity.

In a first aspect, provided herein is a recombinant yeast that has been genetically engineered to exhibit a decreased level of functional PTK2 or SKY1 polypeptide. The recombinant yeast has increased tolerance to ionic liquid toxicity relative to a wild-type yeast or another recombinant yeast not exhibiting a decreased level of functional PTK2 or SKY1 polypeptide. The ionic liquid can be an imidazolium-based ionic liquid. The recombinant yeast can comprise a disabling mutation in a gene encoding a PTK2 or SKY1 polypeptide. The disabling mutation can comprise a deletion of at least a portion of the gene encoding a PTK2 or SKY1 polypeptide, whereby the yeast exhibits a decreased level of functional PTK2 or SKY1 polypeptide. In some cases, the recombinant yeast produces ethanol at an increased rate relative to a wild-type yeast or another recombinant yeast not exhibiting decreased or undetectable levels of functional PTK2 or SKY1 polypeptides. The increased rate of ethanol production can occur under anaerobic conditions. The recombinant yeast can be of the genus *Saccharomyces*. The recombinant yeast can be of the species *Saccharomyces cerevisiae*.

In another aspect, provided herein is a yeast inoculums comprising: (a) a recombinant yeast according to the invention; and (b) a culture medium.

In a further aspect, provided herein is a method for fermenting cellulosic material into ethanol. The method can comprise or consist essentially of contacting an ionic liquid-treated hydrosylate to a recombinant yeast as provided herein or a yeast inoculum of claim as provided herein for a period of time sufficient to allow fermentation of at least a portion of the cellulosic material to ethanol, whereby more cellulosic material is fermented into ethanol in a hydrosylate comprising at least 1% residual ionic liquid than is fermented into ethanol in a hydrosylate comprising at least 1% residual ionic liquid that is not contacted to the recombinant yeast or the yeast inoculum. The ionic liquid-treated hydrosylate can comprise at least 1.5% residual ionic liquid. The ionic liquid-treated hydrosylate can comprise at least 2% residual ionic liquid. The method can further comprise separating the ethanol from fermented cellulosic material. The ionic liquid-treated hydrosylate can comprise xylose. The recombinant yeast can be *Saccharomyces cerevisiae*. The cellulosic material can comprise lignocellulosic biomass. The lignocellulosic biomass can comprise at least one material selected from the group consisting of agricultural residues, wood, municipal solid wastes, paper and pulp industry wastes, and herbaceous crops.

These and other features, aspects, and advantages will become better understood upon consideration of the following detailed description, drawings and appended claims.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIGS. 1A-B depict chemical genomic profiling of ionic liquids. A genome-wide set of deletion mutants were challenged with a specific compound and grown as a pool for several generations. Mutant specific barcodes were then sequenced and compared to control conditions to identify mutants significantly responsive to the chemical stressor.

FIGS. 2A-C present chemical genomic profiling data demonstrating that deletion of PTK2 and SKY1 improves tolerance to 1-ethyl-3-methylimidazolium chloride (EMIM-Cl). (A) Chemical genomic profiling identified 220 mutants significantly resistant to EMIM-Cl. Of these, a deletion mutant of PTK2 was the most significantly resistant, and deletion mutant of SKY1 was the second most significantly resistant, which was confirmed in with single mutant isolates (B). Mitochondrial gene mutants were among the most sensitive, suggesting that the ILs may target the mitochondria to exert toxicity (FIGS. 2A-B). The deletion mutant of PTK2 in the lab strain was resistant to over 5% EMIM-CL.

FIG. 4B is our proposed model for how deletion of PTK2 confers IL tolerance. The imidazolium cation appears toxic to mitochondria. Efflux of protons via Pma1p is coupled with toxic imidazolium cation influx. When PTK2 is deleted, Pma1p is not activated by phosphorylation, and thus there is lower proton efflux and resultant influx of the toxic imidazolium cation. As the toxic cation is thought to target the mitochondria, the effects of ILs are lessened under anaerobic conditions, where mitochondrial function is reduced. There is clear inhibition even under these condition indicating an essential role mitochondria under anaerobic conditions, or a secondary target of the toxic cation.

Figure 1A:
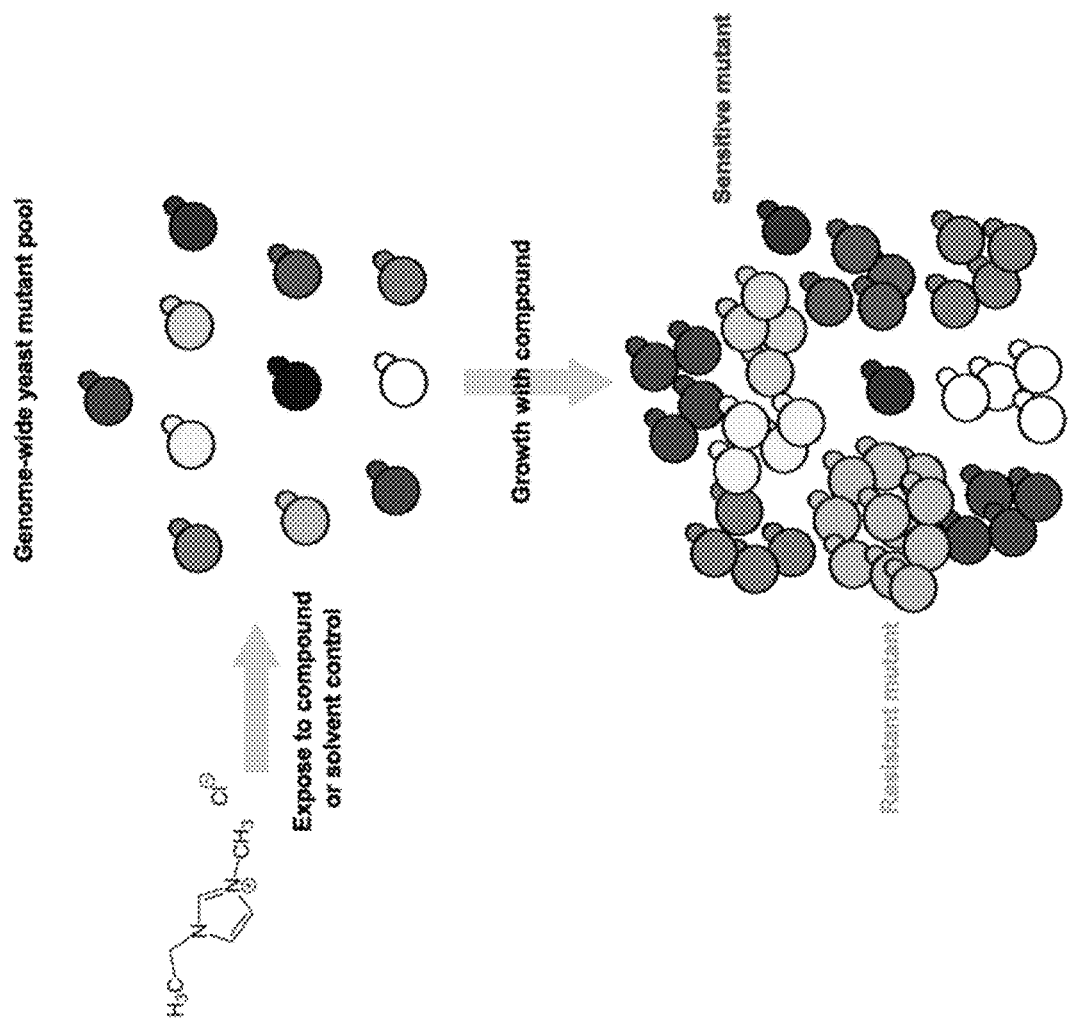

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION OF THE INVENTION

In General

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a," "an," and "the" include plural reference unless the context clearly dictates otherwise. As well, the terms "a" (or "an"), "one or more" and "at least one" can be used interchangeably herein. It is also to be noted that the terms "comprising," "including," and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference in their entirety for all purposes including, for example, describing and disclosing chemicals, cell lines, vectors, animals, instruments, statistical analyses, and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The compositions and methods provided herein will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

The nucleotides which occur in the various nucleotide sequences appearing herein have their usual single-letter designations (A, G, T, C or U) used routinely in the art. In the present specification and claims, references to Greek letters may either be written out as alpha, beta, etc. or the corresponding Greek letter symbols (e.g., α, β, etc.) may sometimes be used.

"Polynucleotide" generally refers to any polyribonucleotide or polydeoxyribonucleotide, which may be unmodified RNA or DNA or modified RNA or DNA. "Polynucleotide" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. As used herein, the term "polynucleotide" also includes DNAs or RNAs as described above that contain one or more modified bases. Thus, DNAs or RNAs with backbones modified for stability or for other reasons are "polynucleotide" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide" as it is employed herein embraces such chemically, enzymatically or metabolically modified forms of polynucleotides, as well as the chemical forms of DNA and RNA characteristic of viruses and cells, including, for example, simple and complex cells. "Polynucleotide" also embraces short polynucleotides often referred to as oligonucleotide(s).

The term "isolated nucleic acid" used in the specification and claims means a nucleic acid isolated from its natural environment or prepared using synthetic methods such as those known to one of ordinary skill in the art. Complete purification is not required in either case. The nucleic acids of the invention can be isolated and purified from normally associated material in conventional ways such that in the purified preparation the nucleic acid is the predominant species in the preparation. At the very least, the degree of purification is such that the extraneous material in the preparation does not interfere with use of the nucleic acid of the invention in the manner disclosed herein. The nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than three separate genes. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene. Specifically excluded from this definition are nucleic acids present in mixtures of clones, e.g., as those occurring in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine, as described in a preceding definition.

Compositions of the Invention

Efficient biochemical conversion and fermentation of renewable lignocellulosic feedstocks is essential for the production of biofuels and other bioproducts from plant materials. While *S. cerevisiae* excel at fermentation of glucose from corn and sugar cane, the fermentation of renewable lignocellulosic biomass presents a significant challenge. Xylose, which is a pentose sugar and a major component of hemicellulose, can comprise almost 30% of total cell wall carbohydrate in grasses. Biomass pretreatments and enzymatic hydrolysis are viable but costly ways of depolymerizing cellulose and hemicellulose fractions of biomass to produce soluble carbohydrates. Large-scale depolymerization cellulose and hemicellulose fractions of biomass is increasingly economically feasible as the cost of hydrolysis reagents drops. Acid-catalyzed hydrolysis methods are generally less expensive than enzyme-catalyzed methods but, in some case, require corrosion-resistant reactors and produce degradation products. Cellulose and hemicellulose fractions can be depolymerized in ionic liquids (ILs), which are organic salts that are liquid at low temperatures by virtue of their low-charge density and low symmetry ions. ILs promote thermocatalytic saccharification through complete solubilization of all lignocellulosic biomass components including lignin, which makes IL-mediated hydrolysis of lignocellulosic biomass a potentially transformative technology for biofuel production. Luterbacher et al., *Science* 343:277-280 (2014); see also Bond et al., *Integrated Catalytic Conversion of γ-Valerolactone to Liquid Alkenes for Transportation Fuels, Science* 26: (2010).

Standard methods of IL-mediated hydrosylation yields hydrolysates that have high sugar levels (glucose and xylose) but also contain residual levels of ILs that are toxic to fermentative microorganisms such as yeast. As shown in Table 1, several ILs have been evaluated for the dissolution of various biomass components under various hydrolysis conditions. Current IL-mediated hydrolysis methods yield hydrosylates comprising about 0.0006% to about 0.85% residual IL (Ouellet et al., *Green Chemistry* 13:2743-2749 (2011)). The present invention is based, at least in part, on the Inventors' discovery of genetic modifications that increase a yeast strain's tolerance for IL toxicity and increase its growth rate in the presence of a broad category of ionic liquids. Accordingly, the compositions and methods provided herein improve the efficiency and cost-effectiveness of ionic liquid-mediated extractions of biofuels and biochemicals from cellulosic materials.

One aspect of the present invention, therefore, relates to eukaryotic host cells genetically engineered for improved tolerance to IL toxicity. In particular, the present invention provides eukaryotic host cells that have been genetically engineered to have enhanced IL toxicity tolerance, enhanced anaerobic and/or aerobic xylose fermentation, and increased ethanol production relative to an unmodified cell or a recombinant cell not genetically engineered as described herein. Modified cells of the present invention are well-suited for the production of fermentable sugars and fermentation products, including ethanol, from processes that use xylose or a combination of xylose and glucose as carbon sources. Moreover, genetically-modified yeast strains provided herein can be used to ferment hydrosylates obtained according to any ionic liquid-based hydrolysis protocol.

TABLE 1

Imidazolium-based Ionic Liquids 1-butyl-3-methylimidazolium tetrafluoroborate
1-butyl-3-methylimidazolium hexafluorophosphate
1-butyl-3-methylimidazolium chloride ([BMIM]Cl)
1-butyl-3-methylimidazolium bromide
1-butyl-3-methylimidazolium dicyanamide
1-butyl-3-methylimidazolium trifluoromethanesulfonate
1-butyl-3-methylimidazolium tris(trifluoromethylsulfonyl)methide
1-butyl-3-methylimidazolium bis(trifluoromethylsulfonyl)imide
1-ethyl-3-methylimidazolium bis(trifluoromethylsulfonyl)imide
1-ethyl-3-methylimidazolium acetate ([EMIM]AcO)
1-ethyl-3-methylimidazolium chloride ([EMIM]Cl)
1-ethyl-3-methylimidazolium dicyanamide
2,3-dimethyl-1-ethylimidazolium bis(trifluoromethylsulfonyl)imide
2,3-dimethyl-1-propylimidazolium bis(trifluoromethylsulfonyl)imide
1-butyl-2,3-dimethylimidazolium tetrafluoroborate
1-butyl-2,3-dimethylimidazolium hexafluorophosphate As used herein. a "host cell" is a cell which has been transformed or transfected, or is capable of transformation or transfection by an exogenous polynucleotide sequence. A host cell that has been transformed or transfected may be more specifically referred to as a "recombinant host cell." A preferred host cell is a host cell that is naturally capable of alcoholic fermentation, preferably, anaerobic alcoholic fermentation. Host cells may also exhibit a high tolerance to ethanol, low pH, organic acids, and/or elevated temperatures. Such characteristics or activities of the host cell may be naturally present in the host cell or may be introduced or modified by genetic modification. Preferred host cells for the present invention include yeast cells, particularly yeast cells of the genus *Saccharomyces*. Preferred yeast species as host cells include *Saccharomyces cerevisiae, S. bulderi, S. barnetti, S. exiguus, S. uvarum, S. diastaticus, K. lactis, K marxianus,* and *Kfragilis*, of which yeast cells of the genus *Saccharomyces* and yeast cells of the species *Saccharomyces cerevisiae* (*S. cerevisiae*) are preferred. Yeasts of the genus *Saccharomyces* possess both a metabolic pathway and a fermentative pathway for respiration.

"Yeasts" are eukaryotic micro-organisms classified in the kingdom Fungi. Most reproduce asexually by budding, although some yeasts undergo sexual reproduction by meiosis. Yeasts are unicellular, although some species with yeast forms may become multi-cellular through the formation of a string of connected budding cells known as pseudohyphae, or false hyphae, as seen in most molds. Yeasts do not form a single taxonomic or phylogenetic grouping. The term "yeast" is often taken as a synonym for *Saccharomyces cerevisiae*, but the phylogenetic diversity of yeasts is illustrated by their assignment to two taxonomic classes of fungi, the ascomycetes and the basidiomycetes.

In exemplary embodiments, a genetically modified yeast of the present invention comprises one or more genetic modifications that reduce or disrupt expression of functional PTK2 (Protein Tyrosine Kinase 2) polypeptide or functional SKY1 (serine-arginine protein-specific kinase) polypeptide. PTK2 and SKY1 are protein kinases that catalyze the transfer of a phosphate group, usually from ATP, to a substrate molecule in *S. cerevisiae*. More specifically, PTK2 is a putative serine/threonine protein kinase that has been implicated in activation of the yeast plasma membrane $H^+$-ATPase (Pma1) in response to glucose metabolism (Goossens et al., *Mol. Cell. Biol.* 20:7654-7661 (2000)). Full-length PTK2 (NCBI Gene ID: 853522; incorporated herein by reference; SEQ ID NO:1) polypeptide is 818 amino acids. SKY1 is involved in regulating proteins involved in mRNA metabolism and cation homeostasis (Erez & Kahana, *Mol. Cell. Biol.* 21:175-184 (2001)). Full-length SKY1 (NCBI Gene ID: 855256; incorporated herein by reference; SEQ ID NO:2) polypeptide is 742 amino acids.

By "delete or disrupt", it is meant that the entire coding region of the gene is eliminated (deletion), or the gene or its promoter and/or terminator region is modified (such as by deletion, insertion, or mutation) such that the gene no longer produces a partially or fully non-functional polypeptide (i.e., lacking enzymatic activity), or produces an enzyme with severely reduced activity. The deletion or disruption can be accomplished by genetic engineering methods, forced evolution or mutagenesis, and/or selection or screening. In exemplary embodiments, a recombinant yeast of the present invention comprises a genetic modification that deletes or disrupts a Ptk2 nucleic acid that encodes PTK2 polypeptide, whereby the genetically modified yeast produces a reduced level of functional PTK2 polypeptide. Yeast genetically modified as such produce no or substantially no functional PTK2 polypeptide. In other embodiments, a recombinant yeast of the present invention comprises a genetic modification that deletes or disrupts a Sky1 nucleic acid that encodes SKY1 polypeptide, whereby the genetically modified yeast produces a reduced level of functional SKY1 polypeptide. Yeast genetically modified as such produce no or substantially no functional SKY1 polypeptide. In some cases, it will be advantageous to genetically modify a host cell to comprise genetic modifications that cause reduced levels of both functional polypeptides, PTK2 and SKY1. Recombinant yeast comprising one or more of the genetic modifications described herein exhibit improve fermentation rates relative to unmodified yeast or yeast not comprising the genetic modifications described herein. Such recombinant yeast also exhibit increased tolerance to IL toxicity and improved growth rates in hydrosylates comprising residual IL following IL-mediated hydrolysis.

It is contemplated that certain additional genetic modifications may be advantageous or necessary to produce other desirable characteristics and/or to enable the yeast cell to produce certain products at industrially-acceptable levels. For example, genetic modifications that reduce or eliminate functional PTK2 polypeptide or functional SKY1 polypeptide can be introduced into *S. cerevisiae* yeast of the GLBRCY128 strain. Yeast of the GLBRCY128 ("Y128") strain were evolved for robust, anaerobic xylose metabolism under industrially relevant conditions and high yields of extracellular ethanol. Forced evolution of the Y128 yeast strain from a background strain designated NRRL YB-210/ GLBRCY0 (Mortimer and Johnston, *Genetics* 113(1):35-43 (1986)), has been described elsewhere. See U.S. Provisional Application No. 61/978,585, filed Apr. 11, 2014.

Accordingly, in some cases, a recombinant yeast of the present invention comprises a genetic modification that deletes or disrupts a Ptk2 nucleic acid that encodes PTK2 polypeptide and further comprises a disabling mutation at a Sky1 locus whereby the mutation results in reduced amounts of functional SKY1 polypeptides.

The degree of IL toxicity to a microorganism such as yeast depends on the yeast's growth conditions. Generally, yeast grown in a minimal medium are more sensitive to chemical stress, while yeast grown in a nutrient-rich medium are more tolerant of chemical stress. Recombinant yeast of the present invention tolerate higher levels of IL relative to a wild type yeast or yeast not comprising a genetic modification described herein when grown in either a nutrient-rich medium or minimal medium. In exemplary embodiments, a recombinant yeast of the present invention that comprises a genetic modification resulting in reduced levels of functional PTK2 polypeptide has significantly more IL tolerance (P<0.05) than a yeast having the same genetic background but having normal levels of functional PTK2 polypeptide, even when growth under industrially relevant conditions in a minimal medium with high sugar loading (osmotically stressful). In general, toxicity is expressed as the "half maximal inhibitory concentration" or "$IC_{50}$." The terms "half maximal inhibitory concentration" and "$IC_{50}$" are used interchangeably and, as used herein, refer to a concentration of the compound that is required to inhibit a given biological or biochemical function by half. In a standard yeast lab strain, the $IC_{50}$ is about 0.33% IL (EMIM-Cl), while a PTK2 deletion mutant in a lab strain background has a $IC_{50}$ of about 5% IL and a SKY1 deletion mutant in a lab strain background has a $IC_{50}$ of about 3.0% IL. In other words, a yeast having a genetic modification (in a standard lab strain background) that eliminates functional PTK2 polypeptide can tolerate IL toxicity wherein IL comprises up to about 5% of the hydrosylate. Similarly, yeast having a genetic modification (in a standard lab strain background) that eliminates functional SKY1 polypeptide can tolerate IL toxicity wherein IL comprises about 3% of the hydrosylate.

The $IC_{50}$ for a genetically modified yeast of the present invention, when grown anaerobically in a minimal medium, is in the range between about 2.0% IL and about 3.0% IL, as compared to an $IC_{50}$ of about 1.0% for unmodified yeast of the xylose-fermenting background strain (Y128). When grown in a nutrient-rich media, yeast of the Y128 xylose-fermenting strain have an $IC_{50}$ of about 0.75% IL, whereas genetically modified yeast strains of the present invention have an $IC_{50}$ of about 2.5% IL (EMIM-Cl). The relative changes in $IC_{50}$ between the unmodified background and the modified yeast are approximately 0.28% (for unmodified) vs. approximately 0.55% (modified) for BMIM-Cl and approximately 0.75% (for unmodified) vs. approximately 2% (modified) for EMIM-Ac.

In some cases, a suitable host yeast cell comprises at least one native gene (a "xylose isomerase gene") that produces an active xylose isomerase enzyme that is capable of catalyzing the interconversion of D-xylose to D-xylulose. Xylose isomerase can also catalyze the interconversion of D-ribose to D-ribulose and D-glucose to D-fructose. The enzyme can be specific to the reduction of xylose or non-specific (i.e., capable of catalyzing the conversion of a range of pentose sugars). In some cases, a suitable host yeast cell is genetically engineered to contain an expression cassette containing *Clostridium phytofermentans* xylose isomerase (CphytoXylA), which can confer anaerobic xylose fermentation by *S. cerevisiae* with additional genetic modifications (see Brat et al., *Applied Environmental Microbiol.* 75:2304 (2009)), driven by the ScerTDH3 promoter. In exemplary embodiments, the expression cassette further comprises ScerTAL1, a Pentose Phosphate Pathway transaldolase enzyme that can improve xylose metabolism when overexpressed (see Ni et al., *Applied Environmental Microbiol.* 73:2061 (2007); Walfridsson et al., *Applied Environmental Microbiol.* 61:4184 (1995)), and SstipXYL3 driven by the ScerPGK1 and ScerTEF2 promoters, respectively. For example, the host yeast cell can comprise a TAL1-XylA-XYL3 gene expression cassette.

Genetic modification of the host cell can be accomplished in one or more steps via the design and construction of appropriate vectors and transformation of the host cell with those vectors. Nucleic acid constructs useful in the invention may be prepared in conventional ways, by isolating the desired genes from an appropriate host, by synthesizing all or a portion of the genes, or combinations thereof. Similarly, the regulatory signals, the transcriptional and translational initiation and termination regions, may be isolated from a natural source, be synthesized, or combinations thereof. The various fragments may be subjected to endonuclease digestion (restriction), ligation, sequencing, in vitro mutagenesis, primer repair, or the like. The various manipulations are well known in the literature and will be employed to achieve specific purposes.

The various nucleic acids and/or fragments thereof may be combined, cloned, isolated and sequenced in accordance with conventional ways. After each manipulation, the DNA fragment or combination of fragments may be inserted into the cloning vector, the vector transformed into a cloning host, e.g., *E. coli*, the cloning host grown up, lysed, the plasmid isolated and the fragment analyzed by restriction analysis, sequencing, combinations thereof, or the like.

Targeted integration can be accomplished by designing a vector having regions that are homologous to the upstream (5'-) and downstream (3'-) flanks of the target gene. Either of both of these regions may include a portion of the coding region of the target gene. The gene cassette (including associated promoters and terminators if different from those of the target gene) and selection markers (with associated promoters and terminators as may be needed) can reside on a vector between the regions that are homologous to the upstream and downstream flanks of the target gene. Targeted cassette insertion can be verified by any appropriate method such as, for example, PCR. A host cell may be transformed according to conventional methods that are known to practitioners in the art. Electroporation and/or chemical (such as calcium chloride- or lithium acetate-based) transformation methods can be used. The DNA used in the transformations can either be cut with particular restriction enzymes or used as circular DNA. Methods for transforming yeast strains are described in WO 99/14335, WO 00/71738, WO 02/42471, WO 03/102201, WO 03/102152 and WO 03/049525; these methods are generally applicable for transforming host cells in accordance with this invention. Other methods for transforming eukaryotic host cells are well known in the art such as from standard handbooks, such as Sambrook and Russel (2001) "Molecular Cloning: A Laboratory Manual (3rd edition)," Cold Spring Harbor Laboratory, Cold Spring Harbor Laboratory Press, or F. Ausubel et al., eds., "Current protocols in molecular biology," Green Publishing and Wiley Interscience, New York (1987).

Any appropriate genetic transformation method can be used to introduce a nucleic acid (e.g., a transgene) into a yeast strain of interest. In some cases, a nucleic acid as described herein is introduced into *S. cerevisiae* yeast by physiological transformation (Buzby et al., *Science* 230:805 (1985)). Linear DNA fragments can be effectively introduced by transformation (Frigaard et al., *Methods in Molecular Biology* 274:325 (2004)), are relatively resistant to host restriction, and are targeted to sites within the chromosome or plasmids by homologous recombination (Cierico et al., *Methods in Mol. Biol.* 362:155-171 (2007)). Alternatively, plasmids capable of replicating in certain yeast (Stinchcomb et al., *PNAS* 77(8):4559-4563 (1980)), bacteria (Cohen et al., *PNAS* 70(11):3240-3244 (1973)), and cyanobacteria (Takeshima et al., *DNA Research* 1:181-189 (1994)) may also be introduced by transformation. For example, shuttle plasmids capable of replicating in both *E. coli* and *S. cerevisiae* yeast may be modified to introduce target nucleic acids or an expression cassette of interest into a host cell. In some cases, transgenes are targeted to the genome.

In another aspect, compositions of the present invention further include yeast inocula comprising recombinant yeast as provided herein. A yeast inoculum of the present invention comprises (a) a recombinant yeast as provided herein and (b) a culture medium. In exemplary embodiments, the recombinant yeast is *S. cerevisiae* and the culture medium is a culture medium comprising yeast extract, peptone, and glucose (e.g., YPD medium), but any culture medium appropriate for culturing yeast strains or stocks can be used. Standard protocols for preparing yeast culture media are available in the art. See, for example, Atlas, Handbook of Microbiological Media, 4th ed. CRC Press (2010). Yeast inocula of the present invention include large-scale preparations of sufficient quantities of viable yeast cells for use in, for example, xylose fermentation and other industrial ethanol-producing methods. When contacted to a IL-treated hydrosylate comprising some level of residual IL, a yeast inoculum of the present invention exhibits improved xylose fermentation rates and increased growth rates relative to a yeast inoculum that does not comprises a recombinant yeast of the present invention.

Recombinant yeast having improved tolerance to imidizolium-based ionic liquids as described herein find use in xylose fermentation processes that use ionic liquids, where extensive purification of the hydrolysate is not required. Recombinant yeast as provided herein also find use as a chassis strain to develop novel biosynthetic pathways (e.g., isobutanol, platform chemicals) for use in ionic liquid hydrolysate fermentations.

Methods of the Invention

The methods provided herein involve the discovery and incorporation of genetic modifications into genes encoding certain polypeptides into a single host organism and the use of those organisms to convert xylose to ethanol. In particular, the present invention provides a method of fermenting cellulosic material comprising the 5-carbon sugar xylose into ethanol, where the method comprises use of a recombinant yeast having enhanced tolerance to IL toxicity relative to wild type yeast or a recombinant yeast not comprising the genetic modifications described herein.

In one aspect, therefore, methods are provided herein for obtaining genetically modified yeast having improved tolerance to imidizolium-based ionic liquids, where the method comprises deleting PTK2 and SKY1, a regulator of ion transport, in a yeast of interest.

In another aspect, provided herein are methods for producing useful fuel or chemical feedstocks, where the method comprises contacting a recombinant yeast as provided herein to a source of xylose and other sugars and maintaining the recombinant yeast appropriate fermentation conditions. The sugars can come from a variety of sources including, but not limited to, cellulosic material. The cellulosic material can be lignocellulosic biomass. As used herein, the term "lignocellulosic biomass" refers to any materials comprising cellulose, hemicellulose, and lignin, wherein the carbohydrate polymers (cellulose and hemicelluloses) are tightly bound to the lignin. Generally, lignocellulosic material for making ethanol is feedstock such as corn stover, which consists of the stems, cobs, and leaves from the corn plants (i.e., the non-grain material). Corn stover is typically shredded by mechanical means and incorporated by tillage into topsoil for decomposition. In addition to lignocellulosic ethanol production from corn stover, other feedstocks such as sorghum, wheat, or another grain can be used. In some cases, lignocellulosic biomass comprises material selected from the group consisting of materials that comprise at least 75% cellulose, cellulose/hemicelluloses, xylose, biomass, and chitin. In other cases. the lignocellulosic biomass comprises at least one material selected from the group consisting of agricultural residues, wood, municipal solid wastes, paper and pulp industry wastes, and herbaceous crops. As used herein, the term "biomass" refers to a renewable energy source, is biological material from living or recently living organisms. As an energy source, biomass can either be used directly, or converted into other energy products such as biofuel. Biomass includes plant or animal matter that can be converted into fibers or other industrial chemicals, including biofuels. Industrial biomass can be grown from numerous types of plants, including miscanthus, switchgrass, hemp, corn, poplar, willow, sorghum, sugarcane, bamboo, and a variety of tree species, ranging from eucalyptus to oil palm (palm oil). Thus, biomass can include wood biomass and non-wood biomass.

In some cases, methods of the present invention include a hydrolyzation step. For example, when cellulosic material is used in the methods disclosed herein, the material can be hydrolyzed to produce a hydrolysate comprising xylose and glucose, which is subsequently contacted to one or more recombinant yeasts of the present invention. As used herein, the term "hydrolysate" refers to a fermentable sugar-containing product produced from cellulosic material (e.g., biomass), typically through pretreatment and saccharification processes. In exemplary embodiments, cellulosic material is pretreated using a solvent comprising one or more ionic liquids (ILs). Such a pretreatment may also comprise one or more physical or chemical treatments such as grinding, ultrasonication, milling, cutting, base treatment such as with ammonia or NaOH, and acid treatment.

In some cases, IL-mediated hydrolysis further comprises an enzymatic saccharification treatment. Enzymatic saccharification typically makes use of an enzyme composition or blend to break down cellulose and/or hemicellulose and to produce an IL-treated hydrolysate containing 6-carbon sugars (e.g., glucose) and 5-carbon sugars (e.g., xylose, arabinose). For review of saccharification enzymes, see Lynd et al., *Microbiol. Mol. Biol. Rev.* 66:506-577 (2002). Saccharification enzymes may be obtained commercially. In some cases, saccharification enzymes may be produced using recombinant microorganisms that have been engineered to express one or more saccharifying enzymes.

Following hydrolyzation, an IL-treated hydrosylate is contacted with one or more of the genetically engineered yeasts disclosed herein (e.g., a yeast strain genetically modified to exhibit reduced amounts of functional PTK2 polypeptide and/or functional SKY1 polypeptide) under conditions suitable for fermentation. Fermentation conditions can comprise aerobic or anaerobic conditions. In exemplary embodiments, a method of the invention comprises contacting under anaerobic conditions a recombinant yeast as provided herein to an IL-treated hydrosylate for a period of time sufficient to allow fermentation of at least a portion of the cellulosic material into ethanol. In exemplary embodiments, a recombinant yeast used according to the methods provided herein is *Saccharomyces cerevisiae*. As used herein, "anaerobic fermentation" refers to a fermentation process run in the absence of oxygen or in which substantially no oxygen is consumed, preferably less than 5, 2.5, or 1 mmol/L/hour, more preferably 0 mmol/L/hour is consumed (i.e., oxygen consumption is not detectable), and where organic molecules serve as both electron donor and electron acceptors. In the absence of oxygen, NADH produced in glycolysis and biomass formation cannot be oxidized by oxidative phosphorylation.

In another aspect, the present invention provides a method of fermenting cellulosic material comprising the 5-carbon sugar xylose into ethanol, where the method comprises use of a recombinant yeast having enhanced tolerance of IL relative to a wild type yeast or a recombinant yeast not comprising the genetic modifications described herein. In particular, the present invention provides a method whereby the rate of fermentation of cellulosic material in an IL-treated hydrosylate to ethanol is increased relative to the fermentation rate of an IL-treated hydrosylate not contacted to a recombinant yeast or yeast inoculum provided by the present invention. In such cases, the method comprises contacting an IL-treated hydrosylate to a recombinant yeast having increased tolerance to IL toxicity, whereby cellulosic material of the contacted hydrosylate is fermented to produce ethanol at an enhanced rate relative to fermentation of an IL-treated hydrosylate that has not been contacted to a recombinant yeast of the present invention.

In some cases, methods of the present invention further comprise an ethanol separation or extraction step. Following conversion of sugars into ethanol, the ethanol can be separated from a fermentation culture using, for example, a standard distillation method or by filtration using membranes or membrane systems known in the art. Methods of separating or extracting are not restricted to those disclosed herein.

Methods of the present invention can be conducted continuously, batch-wise, or some combination thereof.

In another aspect, provided herein are methods for producing fuels and chemical feedstocks from glycerol (or glycerin). Glycerol is a by-product of biodiesel production, which, using a recombinant yeast of the present invention, could be further converted to a fuel or chemical feedstock such as, for example, ethanol, lactic acid, isobutanol, and propanediol. In some cases, the method converts glycerol to ethanol and comprises contacting glycerol to one or more of the genetically engineered yeasts disclosed herein (e.g., a yeast strain genetically modified to exhibit reduced amounts of functional PTK2 polypeptide and/or functional SKY1 polypeptide) under appropriate fermentation conditions. In exemplary embodiments, methods are provided for producing lactic acid from glycerol. In such cases, the method comprises contacting under anaerobic conditions a recombinant yeast provided herein to glycerol for a period of time sufficient to allow fermentation of at least a portion of the glycerol into lactic acid. Lactic acid is in high demand as a chemical feedstock for the biodegradable plastic known as polylactic acid (PLA), a biopolymer that is useful in a variety of applications including packaging material and medical devices (e.g., surgical sutures, orthopedic implants). The raw materials required to manufacture lactic acid are expensive and limit use of PLA. In other cases, the method of converting glycerol into a useful fuel comprises contacting under anaerobic conditions a recombinant yeast as provided herein to glycerol for a period of time sufficient to allow fermentation of at least a portion of the glycerol into ethanol or butanol.

In exemplary embodiments, a recombinant yeast used according to the methods provided herein is *Saccharomyces cerevisiae* (*S. cerevisiae*). Following conversion of glycerol into ethanol, the fuel or chemical feedstock can be separated from a fermentation culture using, for example, a standard distillation method or by filtration using membranes or membrane systems known in the art. Methods of separating or extracting are not restricted to those disclosed or exemplified herein.

Articles of Manufacture

In a further aspect, the present invention provides an article of manufacture containing any one or more of the recombinant yeasts disclosed herein is provided. An article of manufacture can contain one of the microorganisms disclosed herein (e.g., one or more of the yeast strains), or an article of manufacture can contain two or more of the microorganisms disclosed herein. Articles of manufacture disclosed herein also can include, for example, components necessary for growth of the particular microorganism(s).

While the present invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents and alternatives falling within the spirit and scope of the invention as defined by the appended claims.

The present invention will be more fully understood upon consideration of the following non-limiting Examples. All papers and patents disclosed herein are hereby incorporated by reference as if set forth in their entirety.

EXAMPLES

Example 1

Genetic Engineering and Directed Evolution of a *S. cerevisiae* Strain Tolerant to Ionic Liquid (IL) Toxicity Using chemical genomics guided biodesign, we identified 2 genes that are key in mediating IL tolerance of the fermentative yeast *S. cerevisiae*. Chemical genomic profiling of EMIM-Cl identified 220 significantly responsive genes to EMIM-Cl (FIG. 2A; Table 3). Sensitive mutants gave insight into the mode of action of EMIM-Cl and suggested it was toxic to mitochondria. Top sensitive mutants were found to be mitochondrial genes ARG2, HMI1, MCT1, QCR2, RIM1, and SHE9 (Table 2). ARG2 is mitochondrial enzyme that catalyzes the first step in the biosynthesis of the arginine precursor ornithine (Abadjieva et al., 2001). HMI1 is a mitochondrial DNA helicase (Lee et al., 1999). MCT1 is a component of mitochondrial fatty acid synthase (Schneider et al., 1997). QCR2 is a subunit of ubiquinol cytochrome-c reductase, a component of the mitochondrial inner membrane electron transport chain. RIM1 is ssDNA-binding protein essential for mitochondrial genome maintenance (Li et al., 1998, p. 1). We tested the top 2 sensitive and resistant mutants (QCR2, ARG2, PTK2, and SKY1), to confirm sensitivity or resistance of the individual mutants (FIG. 2B). Further, when we correlated the chemical genomic profile of EMIM-Cl to existing chemical genomic datasets (Parsons et al., 2006), we found it had the highest correlation with the mitochondria de-polarization agent valinomycin ($p<0.001$). Taken together, it suggests EMIM-Cl is toxic to mitochondrial function.

Figure 3:
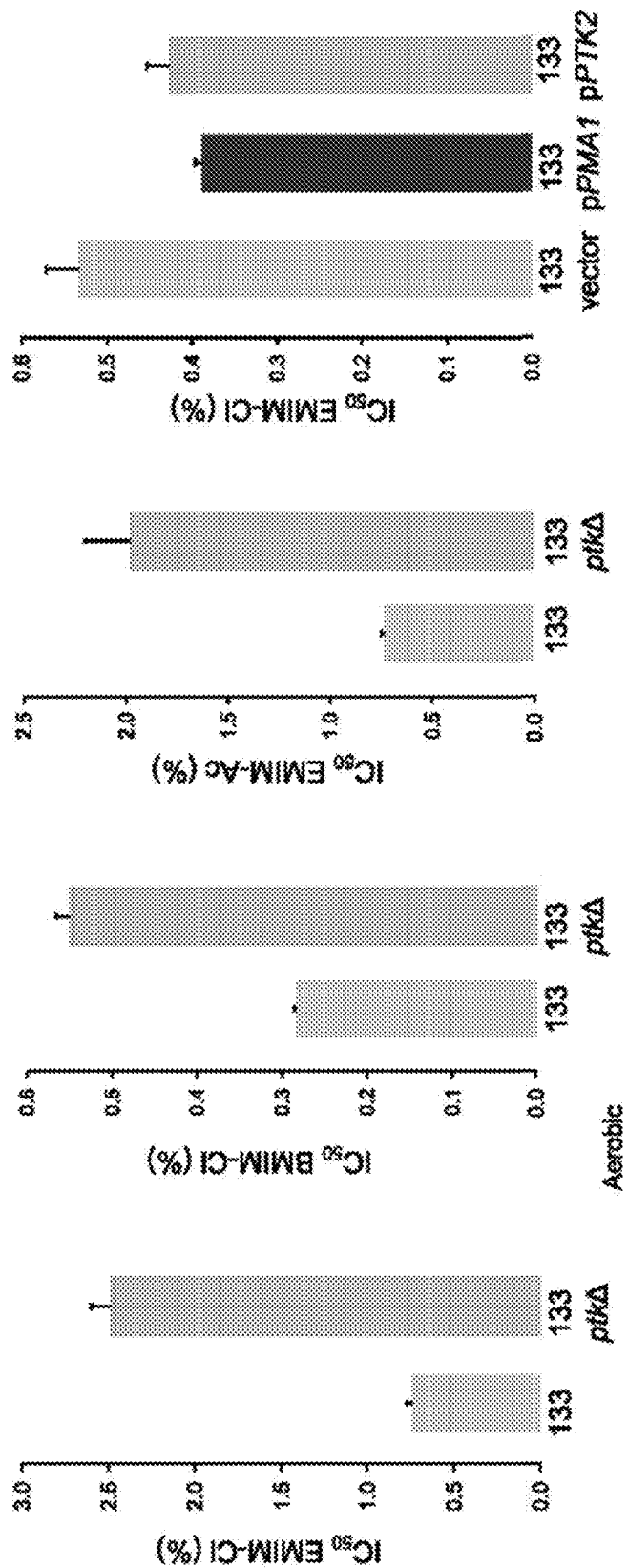
FIG. 3 demonstrates performance of the PTK2 deletion mutant in the GLBRC xylose-fermenting yeast strain in the presence of various imidazolium ionic liquids. Deletion of PTK2 in the xylose-fermenting yeast strain Y133 conferred significantly greater tolerance of EMIM-Cl, BMIM-Cl, and EMIM-Ac ($p<0.01$). Overexpression of the $H^+$-ATPase PMA1 confers sensitivity to EMIM-Cl. Overexpression of the essential proton pump Pma1p, which is regulated by Ptk2p, significantly reduced EMIM-Cl tolerance. Overexpression of PTK2 also increased EMIM-Cl sensitivity but not significantly. Mean±S.E., n=3.

We determined that ionic liquids were more toxic to cells grown on glycerol compared to glucose (FIG. 3A). Using microscopy, we explored the effect of ionic liquids on mitochondria. Cultures treated with EMIM-Cl displayed a dose-dependent effect on staining of active mitochondria, as determined with SYTO® 16 (Life Technologies) green fluorescent nucleic acid stain, which preferentially binds yeast mitochondrial nucleic acids (FIG. 3B). Untreated cells had normal mitochondrial morphology, and at higher doses, mitochondria structures in cells disappeared indicating a loss of functional mitochondria. Finally, we used FACS analysis with the stain 3,3-Dioctadecyloxacarbocyanine perchlorate ("DiO"), which has differential fluorescence depending on mitochondrial membrane potential. In the presence of ionic liquids, we observed a fluorescence shift of DiO, indicating reduced mitochondrial membrane potential (FIGS. 3C-D). Valinomycin was used as a positive control. Hydroxyurea and benomyl were included as negative control agents that causes cell death through a mechanism unrelated to the mitochondria.

TABLE 2

Deletion Mutants Sensitive to EMIM-Cl

| Gene | Fold change | Adjusted P-value | Gene description |
|---|---|---|---|
| QCR2 | 0.19498 | 7.45E−26 | Subunit 2 of ubiquinol cytochrome-c reductase (Complex III); Complex III is a component of the mitochondrial inner membrane electron transport chain |
| ARG2 | 0.170584 | 2.22E−25 | Acetylglutamate synthase (glutamate N-acetyltransferase); mitochondrial enzyme that catalyzes the first step in the biosynthesis of the arginine precursor ornithine |
| RIM1 | 0.197448 | 7.98E−25 | ssDNA-binding protein essential for mitochondrial genome maintenance; involved in mitochondrial DNA replication |
| SHE9 | 0.201427 | 2.67E−23 | Protein required for normal mitochondrial morphology; mitochondrial inner membrane protein |
| LYS5 | 0.182056 | 2.67E−23 | Phosphopantetheinyl transferase involved in lysine biosynthesis |
| YPT7 | 0.158357 | 2.67E−23 | Rab family GTPase; GTP-binding protein of the rab family; required for homotypic fusion event in vacuole inheritance, for endosome-endosome fusion |
| MCT1 | 0.15756 | 6.69E−23 | Predicted malonyl-CoA: ACP transferase; putative component of a type-II mitochondrial fatty acid synthase that produces intermediates for phospholipid remodeling |
| HMI1 | 0.193927 | 1.18E−22 | Mitochondrial inner membrane localized ATP-dependent DNA helicase; required for the maintenance of the mitochondrial genome |
| GAL1 | 0.196168 | 2.48E−22 | Galactokinase; phosphorylates alpha-D-galactose to alpha-D-galactose-1-phosphate in the first step of galactose catabolism |
| PUF4 | 0.186306 | 1.03E−19 | Member of the PUF protein family |

Deletion of Kinases Involved in Ion Homeostasis Confers IL Tolerance

Figure 4A:
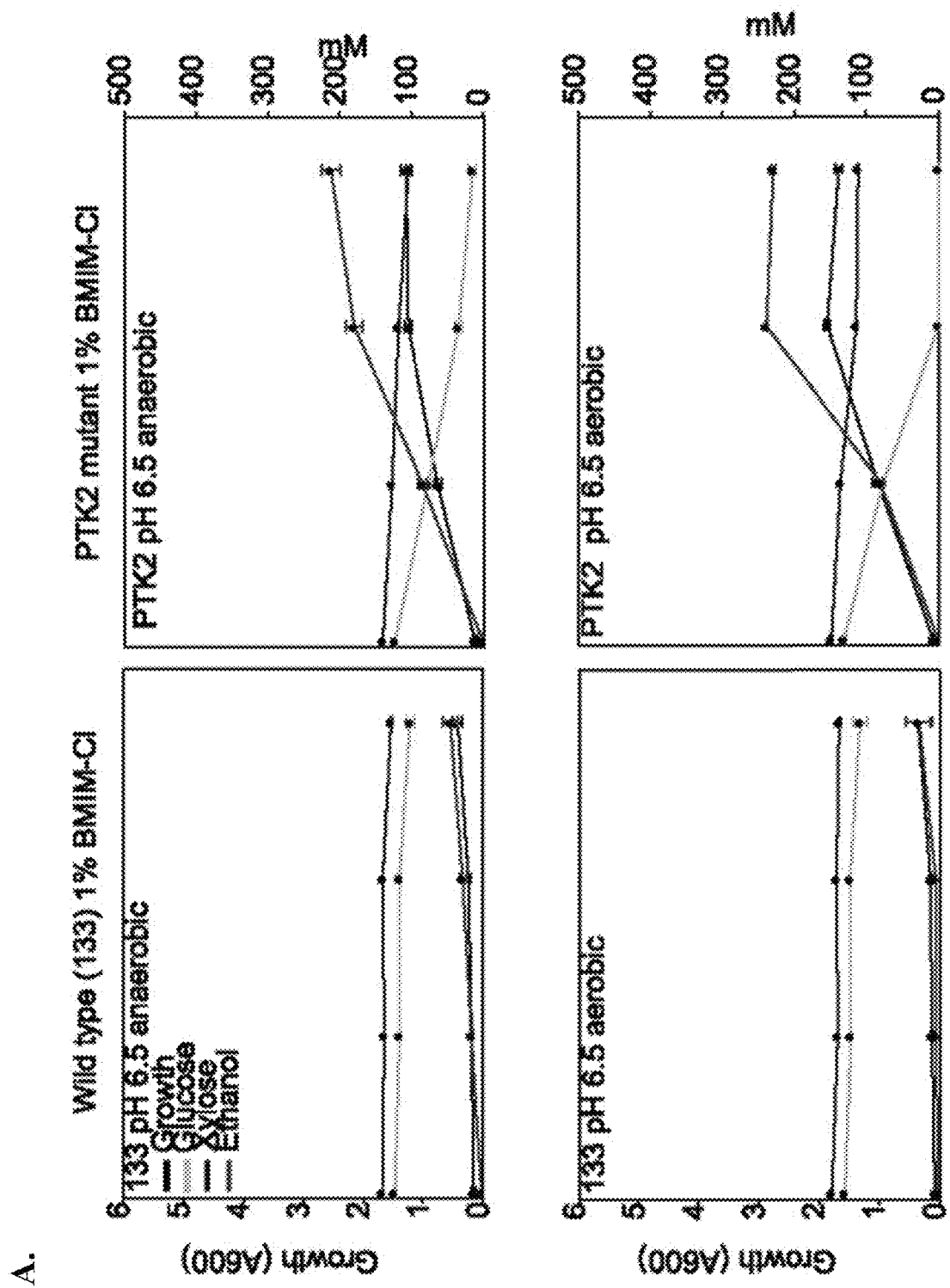
FIGS. 4A-B demonstrate that under both aerobic and anaerobic conditions, the PTK2 deletion confers greater tolerance and has greater fermentative capacity in the presence of 1% BMIM-Cl (A).

Resistant mutants uncovered by chemical genomics can identify points to rationally engineer resistance. The top resistant deletion mutant was PTK2 (FIG. 2A). PTK2 is a putative serine/threonine protein kinase involved in regulation of ion transport across plasma membrane (Erez and Kahana, 2002; Kaouass et al., 1997). This mutant had a 12-fold positive fold-change ($p=1e^{-74}$) in fitness in the presence of EMIM-Cl, indicating greater growth than all other strains. The second most significant resistant strain was a deletion mutant of SKY1 (fold change=4.5, $p=1e^{-21}$), which is functionally similar to PTK2 and is a protein kinase involved in regulating proteins involved in cation homeostasis (Erez and Kahana, 2002). We confirmed resistance of these individual mutants (FIG. 2B). The PTK2 mutant had a significantly higher $IC_{50}$ score than the WT (FIG. 4A). Mutants of YPT7 were among the most sensitive, deletion of this gene has been shown to decrease ionic stress tolerance of zinc and calcium ions (Kucharczyk et al., 2000).

Figure 4B:
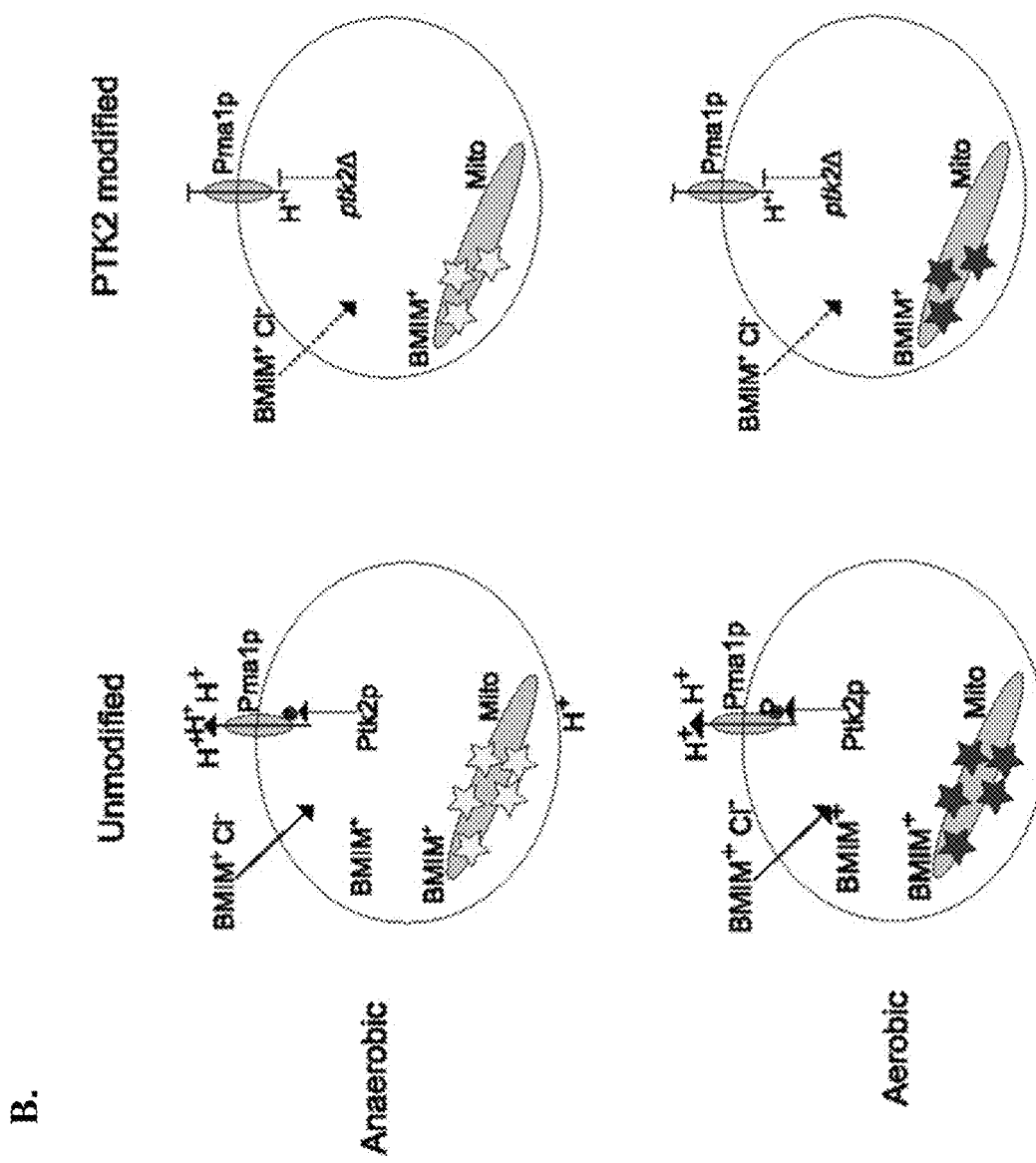
Figure 5:
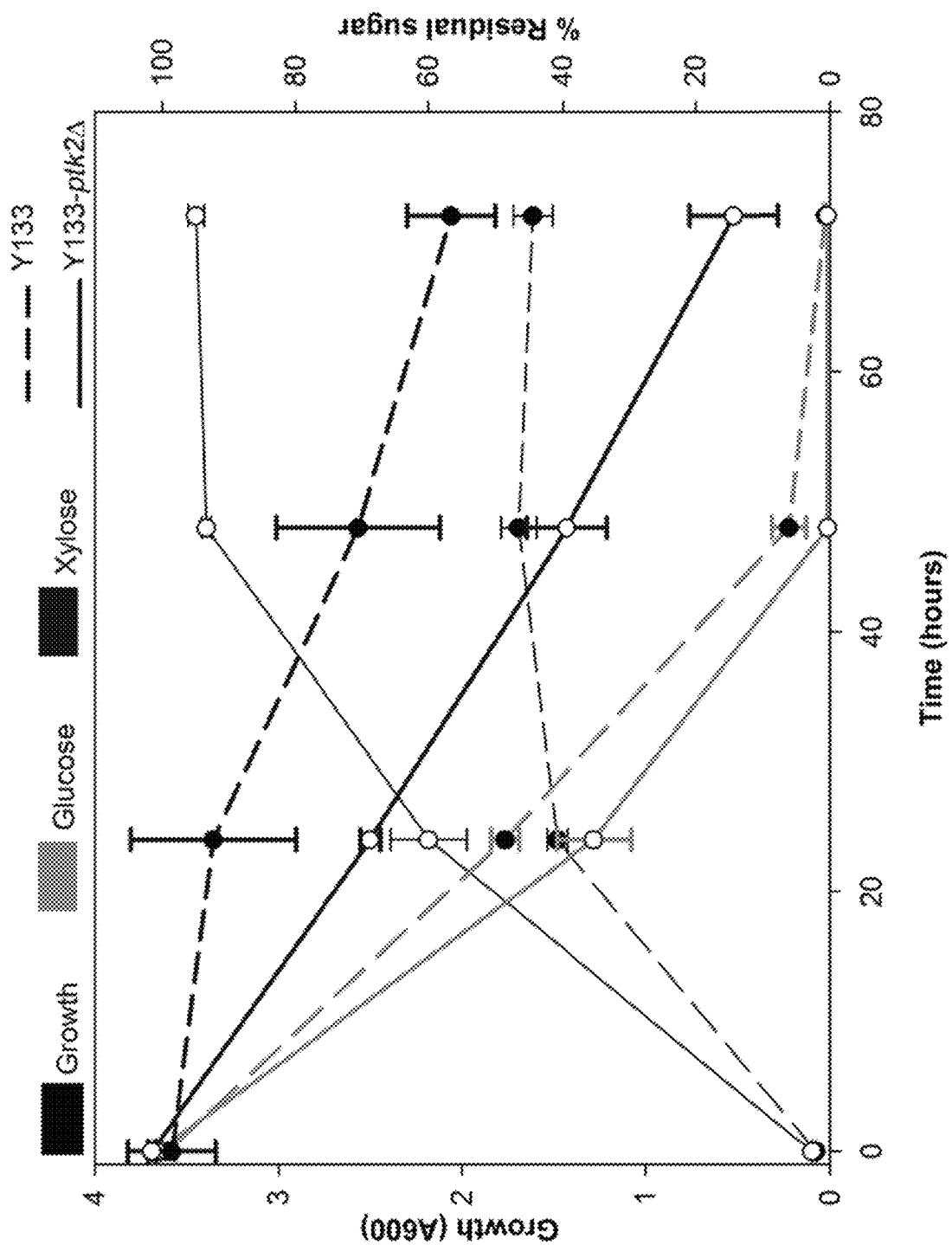
FIG. 5 presents fermentation data for growth, sugar conversion, and ethanol production of Y133 and Y133 ptk2Δ in the presence of 1% EMIM-Cl.

As PTK2 was the most resistant mutant in both the initial screen and validations, we focused on this gene. We deleted PTK2 in our xylose fermenting yeast GLBRCY133 (Parreiras et al.,2014). The half-maximal inhibition concentration (IC50) of EMIM-Cl in Y133 yeast was 0.76%, whereas the PTK2 mutant had an IC50 of 2.4% (FIG. 4B). This modification also conferred tolerance to BMIM-Cl and EMIM-Ac, suggesting all have a similar mode of toxicity that is mediated by PTK2. We found the mutant also significantly improved sugar conversion (glucose and xylose) and ethanol production in the presence of 1% EMIM-Cl (FIG. 5). PTK2 has been shown to positively regulate the essential proton efflux pump Pma1p. Further, PMA1 is also regulated by IXR1, which was the 5th most significant ($p=2.7e^{-11}$) resistant mutant (Table 3). We tested if over expression of PMA1 could cause EMIM-Cl sensitivity, and as predicted increased expression of PMA1 caused a significant decrease in EMIM-Cl tolerance ($p<0.01$). Overexpression of PTK2 also reduced EMIM-Cl tolerance, but not significantly. This suggests that PMA1 mediates the toxicity of ionic liquids via its role in pH regulation, and decreasing the activity of Pma1p through deletion of PTK2 can confer resistance to imidazolium ionic liquids. SKY1 is not known to interact with PMA1, and it has been shown to have a mode of action independent of PTK2 in ion regulation despite similar phenotypes (Eraso et al., 2006). We found a strong pH effect on IL toxicity. At near neutral pH (pH 6.5), the effects of EMIM-Cl were much greater, yet there was not a significant difference between the Y133 and the Y133 ptk2Δ strain at a lower pH (pH 5.0) (FIG. 5). In the absence of EMIM-Cl, the 2 strains had near equivalent growth (FIG. 5).

Taken together, we would propose the following model for the mechanism of toxicity of imidazolium ionic liquids, as well as alleviation by deletion of PTK2. As the ILs seem to exert toxicity on the mitochondria, we propose IL toxicity would be greatest under aerobic conditions, rather than anaerobic where mitochondrial activity is diminished. Secondly, we propose that the toxic imidazolium cation enters the cell at points of active cation efflux (such as H+ efflux by Pma1p). In this case, IL toxicity would be further diminished under in low pH media where Pma1p is less active. aerobic/anaerobic and pH6.5/pH5.0 conditions in the presence of BMIM-Cl (a more toxic IL). The data supports our proposed model. The greatest toxicity occurs at near neutral pH under aerobic conditions in the WT strain. The WT still performs poorly under aerobic conditions, but growth is slightly better. At pH 5.0, the effects of the ILs are reduced but the PTK2 mutant performs better in both aerobic and anaerobic condition. In support of this model, we found the effects of ILs on mitochondrial membrane potential were lessened in the ptk2Δ strain.

Materials & Methods

Compounds, initial screening, and $IC_{50}$ determination: Compounds tested were purchased from Sigma-Aldrich. Cells of S. cerevisiae (MATαpdr1Δ::natMXpdr3Δ::KI.URA3 snq2Δ::KI.LEU2 can1Δ::STE2pr-Sp_his5 lyp1Δhis3Δ1 leu2Δ0 ura3Δ0 met15Δ0), referred to as control strain, were grown in 200 μl cultures at 30° C. in YPD, with a drug or DMSO control. Plates were read on a TECAN M1000 over a 48 hour growth period. The specific growth rate was calculated using GCAT analysis software (available at cat3-pub.glbrc.org on the World Wide Web) (Sato et al., 2013). When presented, $IC_{50}$ values for growth inhibition were calculated from triplicate 8 point dose curves and SigmaPlot 12.0. When presented, error bars are mean±standard error (S.E.) of at least 3 replicates.

Chemical genomic analysis: Chemical genomic analysis of poacic acid was performed as described as described previously (Fung et al., 2013; Parsons et al., 2006). The tested yeast deletion collection had 4000 strains using the genetic background described in Andrusiak (2012). The optimal inhibitory concentration of poacic acid for chemical genomic profiling (70-80% growth versus solvent control in YP-galactose media after 24 hours of growth) was determined using an 8 point dose curve. A concentration of 88 µg/ml inhibited growth within this range. 200 µl cultures of the pooled, deletion collection of S. cerevisiae deletion mutants were grown with 88 µg/ml poacic acid or a DMSO control in triplicate for 48 hours at 30° C. Genomic DNA was extracted using the Epicentre MasterPure™ Yeast DNA purification kit. Mutant-specific molecular barcodes were amplified with specially designed multiplex primers (Smith et al., 2009). The barcodes were sequenced using an Illumina MiSeq. Three replicates of each condition (poacic acid vs. DMSO) were sequenced. One DMSO control was lost due to poor sequencing reads. The barcode counts for each yeast deletion mutant in the presence of poacic acid were normalized against the DMSO control conditions to define sensitivity or resistance of individual strains. To determine a p-value for each top sensitive and resistant mutant, we used the EdgeR package (Robinson et al., 2014, 2010). A Bonferroni-corrected hypergeometric distribution test was used to search for significant enrichment of GO terms among the top 10 sensitive and resistant deletion mutants (Boyle et al., 2004). To understand the pathways that were most affected by poacic acid we developed a protein complex/pathway score based on the summation of the z-scores for each complex/pathway (Pathway z-score). Correlation of the chemical genomic profile of poacic acid with the yeast genetic interaction network to was done as described in Costanzo et al. (2010).

TABLE 3

Responsive EMIM-Cl Deletion Mutants

| ORF | Fold Change | Adjusted P--value |
|---|---|---|
| PTK2 | 12.02580613 | 1.00E-74 |
| QCR2 | 0.194980443 | 7.45E-26 |
| ARG2 | 0.170584492 | 2.22E-25 |
| RIM1 | 0.197447841 | 7.98E-25 |
| SHE9 | 0.201426955 | 2.67E-23 |
| LYS5 | 0.182056228 | 2.67E-23 |
| YPT7 | 0.158356669 | 2.67E-23 |
| MCT1 | 0.157560266 | 6.69E-23 |
| HMI1 | 0.193926778 | 1.18E-22 |
| GAL1 | 0.196168114 | 2.48E-22 |
| SKY1 | 4.547039983 | 8.72E-21 |
| PUF4 | 0.186305965 | 1.03E-19 |
| SWS2 | 0.182120822 | 2.33E-18 |
| VPS24 | 0.190770275 | 2.33E-18 |
| COQ2 | 0.224014905 | 4.40E-18 |
| IMG2 | 0.195088678 | 4.40E-18 |
| RPN14 | 0.179147805 | 3.07E-17 |
| YGL010W | 0.279105407 | 1.39E-16 |
| LEU1 | 0.191102193 | 1.39E-16 |
| TRP1 | 0.184520001 | 1.39E-16 |
| YGR022C | 0.218835697 | 6.93E-16 |
| NHP10 | 0.218719506 | 1.52E-15 |
| ECT1 | 0.190663421 | 1.55E-15 |
| GCV1 | 0.218285637 | 3.40E-15 |
| RAD57 | 0.276130823 | 1.24E-13 |
| FMT1 | 0.178006363 | 1.32E-13 |
| SGE1 | 2.65402935 | 3.72E-13 |

TABLE 3-continued

Responsive EMIM-Cl Deletion Mutants

| ORF | Fold Change | Adjusted P--value |
|---|---|---|
| ATE1 | 0.292196821 | 1.85E-12 |
| HIS6 | 0.198723718 | 2.31E-12 |
| FEN1 | 4.69165376 | 3.57E-12 |
| YDL012C | 0.36442804 | 1.22E-11 |
| COX10 | 0.266761544 | 1.40E-11 |
| LIP2 | 0.221691215 | 1.99E-11 |
| CBC2 | 0.234704258 | 2.14E-11 |
| IXR1 | 2.699554208 | 2.70E-11 |
| LYS12 | 0.195058513 | 3.13E-11 |
| SLM3 | 0.208236171 | 5.03E-11 |
| TOF1 | 0.280631249 | 6.94E-11 |
| YNL171C | 3.468541252 | 3.27E-10 |
| SOK1 | 0.366775393 | 4.69E-10 |
| BUD21 | 0.305919651 | 1.81E-09 |
| COG7 | 0.319888577 | 1.87E-09 |
| AIM22 | 0.278105636 | 2.80E-09 |
| BUB1 | 0.245581688 | 5.02E-09 |
| MET18 | 2.225601034 | 8.98E-09 |
| RPL22A | 3.036427183 | 9.48E-09 |
| RMD1 | 0.360663343 | 1.27E-08 |
| LRP1 | 2.696512271 | 1.59E-08 |
| VMS1 | 2.244395124 | 2.25E-08 |
| PMP3 | 0.173511422 | 2.61E-08 |
| GSC2 | 0.226593198 | 2.61E-08 |
| URE2 | 2.54477019 | 3.98E-08 |
| SLM6 | 0.22764663 | 4.24E-08 |
| YCL062W | 0.088564158 | 4.86E-08 |
| RAD27 | 4.137697691 | 8.61E-08 |
| CHD1 | 0.414164421 | 9.98E-08 |
| PTC1 | 0.333165584 | 9.99E-08 |
| RPS6A | 2.11747234 | 1.65E-07 |
| HIS7 | 0.391540398 | 2.06E-07 |
| PMT2 | 2.376491542 | 2.97E-07 |
| SLX5 | 0.384494624 | 6.43E-07 |
| RPS24A | 2.063559947 | 8.12E-07 |
| BRP1 | 1.802482997 | 1.75E-06 |
| VPS4 | 0.284949379 | 2.12E-06 |
| ARG4 | 0.398876145 | 3.03E-06 |
| YOL050C | 1.947624117 | 5.24E-06 |
| FPS1 | 1.813406111 | 5.90E-06 |
| RRP6 | 2.26193037 | 1.32E-05 |
| TMA20 | 1.751522457 | 2.92E-05 |
| BEM1 | 2.226615924 | 3.36E-05 |
| YMR010W | 0.530177671 | 4.18E-05 |
| OST3 | 2.239424373 | 4.88E-05 |
| SUB1 | 1.876097999 | 4.88E-05 |
| RPS1B | 2.497511638 | 4.95E-05 |
| YER156C | 2.550929037 | 0.00010485 |
| SKI3 | 1.761177402 | 0.000117522 |
| DSF2 | 1.855754507 | 0.000166238 |
| RRP8 | 3.09657616 | 0.000184522 |
| RPL35B | 2.190724155 | 0.000244477 |
| WSS1 | 0.314533733 | 0.000247709 |
| ALG5 | 1.752873331 | 0.000248039 |
| GYP1 | 0.372116022 | 0.00027683 |
| RPS19B | 2.407243288 | 0.000277827 |
| RXT2 | 1.617177157 | 0.000277827 |
| ALG9 | 1.715781217 | 0.000295323 |
| MAF1 | 0.21296766 | 0.000342149 |
| TPS1 | 0.541150238 | 0.000348396 |
| TMA23 | 2.386103482 | 0.000375631 |
| PUB1 | 2.278111017 | 0.000388778 |
| AIM1 | 0.569911935 | 0.000446799 |
| SFA1 | 0.242790741 | 0.000564656 |
| EAF1 | 2.42399159 | 0.00058625 |
| BUL1 | 1.731997329 | 0.000596426 |
| HPM1 | 1.74196114 | 0.000731519 |
| LYS2 | 0.462150565 | 0.000731519 |
| OLA1 | 1.644826773 | 0.00083587 |
| YLR279W | 0.5779028 | 0.000904842 |
| REI1 | 2.167869866 | 0.000946346 |
| RHO2 | 1.785203065 | 0.000946346 |
| PMT1 | 1.711961271 | 0.001016251 |
| DAN1 | 0.578606071 | 0.001046222 |
| GRX2 | 0.339437544 | 0.001138368 |

TABLE 3-continued

Responsive EMIM-Cl Deletion Mutants

| ORF | Fold Change | Adjusted P-value |
|---|---|---|
| TOP1 | 1.759222352 | 0.001176807 |
| DIA2 | 2.886364444 | 0.001179284 |
| RPL24B | 2.085646194 | 0.001194221 |
| YSP2 | 1.61808494 | 0.001333724 |
| RPS28B | 2.087820172 | 0.001381818 |
| ARX1 | 1.688293446 | 0.00139627 |
| UPF3 | 1.609815095 | 0.001406756 |
| DOA1 | 1.661240555 | 0.001419772 |
| YLR194C | 0.590930984 | 0.001647096 |
| SVL3 | 0.384738659 | 0.001647096 |
| NMD2 | 1.613751821 | 0.001838007 |
| YDL172C | 1.636215323 | 0.001979281 |
| ROM2 | 2.197687749 | 0.00202286 |
| BAP2 | 1.689341645 | 0.002053442 |
| AVT5 | 1.933438849 | 0.002169373 |
| PPM1 | 0.344370161 | 0.002497633 |
| CTF4 | 2.670273136 | 0.002615534 |
| DEP1 | 2.105683098 | 0.002645979 |
| YIL141W | 1.52407909 | 0.00283954 |
| PUF6 | 1.747601473 | 0.003076765 |
| IST3 | 1.898889958 | 0.003076765 |
| LYS14 | 0.39835021 | 0.003165432 |
| VPS38 | 1.666224043 | 0.00319675 |
| SIN3 | 2.019847313 | 0.003320158 |
| YOL162W | 0.553685477 | 0.003825296 |
| IRA2 | 0.407629512 | 0.00400892 |
| DPB3 | 1.946383305 | 0.004280181 |
| SWI6 | 1.901930869 | 0.004764991 |
| RPS10A | 2.351123012 | 0.004772874 |
| TYE7 | 0.485944749 | 0.004780117 |
| CAT5 | 0.440489553 | 0.004886977 |
| SSK2 | 1.578877231 | 0.00553311 |
| UBC4 | 1.541297429 | 0.005629761 |
| YIR044C | 0.572336777 | 0.0059254 |
| YIH1 | 1.761780624 | 0.006448317 |
| RPL19B | 1.559626518 | 0.006528987 |
| SAP155 | 1.703982839 | 0.00665084 |
| MF(ALPHA)2 | 0.615365791 | 0.006853742 |
| YHB1 | 0.561069189 | 0.006853742 |
| SUR4 | 2.535246198 | 0.007067883 |
| RPL11B | 1.724953433 | 0.007472428 |
| ERF2 | 1.47738195 | 0.007982127 |
| RPL19A | 1.87520079 | 0.008474767 |
| LIA1 | 1.621389964 | 0.008850898 |
| YBR090C | 0.588188337 | 0.010006037 |
| SPS4 | 0.56584427 | 0.010260545 |
| DBP3 | 1.708790709 | 0.011446367 |
| RPS18B | 1.743280408 | 0.012283338 |
| YMR193C-A | 1.86685344 | 0.012510503 |
| MEI4 | 1.592093298 | 0.012523556 |
| RRI1 | 0.615146728 | 0.012523556 |
| YDL118W | 1.521883558 | 0.013046813 |
| PEX32 | 2.102687482 | 0.013102827 |
| BNI4 | 1.66543388 | 0.013262055 |
| HIR2 | 0.458720353 | 0.013408531 |
| ZDS1 | 0.602599615 | 0.014784078 |
| YPL205C | 1.523379369 | 0.015985809 |
| AVT3 | 1.574572994 | 0.015985809 |
| YPS7 | 1.508222236 | 0.016011372 |
| TSR2 | 1.940216199 | 0.016250456 |
| DBF2 | 1.926717732 | 0.016434754 |
| SAY1 | 1.592356536 | 0.017368902 |
| BUD8 | 0.603363321 | 0.017717293 |
| SAP185 | 0.649008208 | 0.017909675 |
| UBP14 | 1.534013542 | 0.018019346 |
| YPR130C | 0.526344103 | 0.018019346 |
| YGR237C | 0.549580524 | 0.018245362 |
| APM3 | 0.522204691 | 0.018245362 |
| RNP1 | 1.49466885 | 0.018245362 |
| TRP2 | 1.685315095 | 0.01871036 |
| RCR1 | 0.450815237 | 0.019050835 |
| YLR434C | 1.500094892 | 0.020825241 |
| SNC2 | 1.57346887 | 0.020886503 |
| YDR352W | 0.588824651 | 0.020886503 |
| COX23 | 0.587047361 | 0.021578429 |
| SEC66 | 2.430760624 | 0.021578429 |
| YAR028W | 1.704403202 | 0.023336882 |
| FYV1 | 1.764880543 | 0.023336882 |
| HAL5 | 0.587197405 | 0.024205854 |
| VPS21 | 1.819782964 | 0.024205854 |
| MRC1 | 1.773378288 | 0.024879254 |
| YMR259C | 0.677558503 | 0.024879254 |
| RPS8A | 1.995545086 | 0.024879254 |
| FYV10 | 1.464914375 | 0.025159395 |
| VPS72 | 0.509225903 | 0.02733555 |
| NGL3 | 0.671907863 | 0.027690877 |
| SDS3 | 1.586060389 | 0.027690877 |
| YMR086W | 0.499097245 | 0.02818714 |
| RPS21B | 1.883670596 | 0.028783922 |
| FDC1 | 0.626868071 | 0.02931875 |
| IES2 | 2.113942593 | 0.02931875 |
| TIR2 | 1.536079747 | 0.030313892 |
| THI20 | 0.459550385 | 0.031142813 |
| VPS27 | 1.573153664 | 0.031310338 |
| ZRG8 | 1.460275931 | 0.031787495 |
| YCR087C-A | 1.607824918 | 0.032567932 |
| COQ10 | 1.641212911 | 0.032567932 |
| KSS1 | 1.404097911 | 0.033407793 |
| IRC18 | 0.661991855 | 0.033549878 |
| RPL40B | 1.554295132 | 0.03544702 |
| PSY4 | 0.597826697 | 0.037614217 |
| SUR2 | 0.664034566 | 0.037614217 |
| URM1 | 1.503096311 | 0.038240128 |
| VHS3 | 1.464054866 | 0.040352936 |
| NAM7 | 1.457064937 | 0.040729076 |
| GBP2 | 1.553440254 | 0.042661626 |
| YDR474C | 0.610716369 | 0.045531097 |
| RPL24A | 2.157465683 | 0.046344723 |
| YGL024W | 3.064854234 | 0.046344723 |
| ARK1 | 0.433074326 | 0.047934054 |
| YNL226W | 2.120057649 | 0.048474052 |
| ULA1 | 0.678863479 | 0.048474052 |
| YAL058C-A | 1.427986652 | 0.048474052 |
| MLP2 | 0.614439126 | 0.048474052 |
| ELP2 | 1.640620535 | 0.048742335 |
| GAL7 | 1.570747272 | 0.049180466 |
| TUM1 | 1.437040713 | 0.04931037 |

The present disclosure incorporates by reference the article "Mechanism of Imidazolium Ionic Liquids Toxicity in *Saccharomyces cerevisiae* and Rational Engineering of a Tolerant, Xylose-Fermenting Strain" Dickinson et al. *Microb Cell Fact* (2016) 15:17 (including supplementary materials and methods).

REFERENCES

Abadjieva, A., Pauwels, K., Hilven, P., Crabeel, M., 2001. A new yeast metabolon involving at least the two first enzymes of arginine biosynthesis: acetylglutamate synthase activity requires complex formation with acetylglutamate kinase. J. Biol. Chem. 276, 42869-42880.

Almeida, J. R., Modig, T., Petersson, A., Hähn-Hägerdal, B., Lidén, G., Gorwa-Grauslund, M. F., 2007. Increased tolerance and conversion of inhibitors in lignocellulosic hydrolysates by *Saccharomyces cerevisiae*. J. Chem. Technol. Biotechnol. 82, 340-349.

Andrusiak, K., 2012. Adapting *S. cerevisiae* Chemical Genomics for Identifying the Modes of Action of Natural Compounds (Thesis).

Binder, J. B., Raines, R. T., 2010. Fermentable sugars by chemical hydrolysis of biomass. Proc. Natl. Acad. Sci. 107, 4516-4521. doi:10.1073/pnas.0912073107.

Boyle, E. I., Weng, S., Gollub, J., Jin, H., Botstein, D., Cherry, J. M., Sherlock, G., 2004. GO::TermFinder—open source software for accessing Gene Ontology information and finding significantly enriched Gene Ontology terms associated with a list of genes. Bioinformatics 20, 3710-3715. doi:10.1093/bioinformatics/bth456.

Costanzo, M., Baryshnikova, A., Bellay, J., Kim, Y., Spear, E. D., Sevier, C. S., Ding, H., Koh, J. L. Y., Toufighi, K., Mostafavi, S., Prinz, J., St. Onge, R. P., VanderSluis, B., Makhnevych, T., Vizeacoumar, F. J., Alizadeh, S., Bahr, S., Brost, R. L., Chen, Y., Cokol, M., Deshpande, R., Li, Z., Lin, Z.-Y., Liang, W., Marback, M., Paw, J., San Luis, B.-J., Shuteriqi, E., Tong, A. H. Y., van Dyk, N., Wallace, I. M., Whitney, J. A., Weirauch, M. T., Zhong, G., Zhu, H., Houry, W. A., Brudno, M., Ragibizadeh, S., Papp, B., Pal, C., Roth, F. P., Giaever, G., Nislow, C., Troyanskaya, O. G., Bussey, H., Bader, G. D., Gingras, A.-C., Morris, Q. D., Kim, P. M., Kaiser, C. A., Myers, C. L., Andrews, B. J., Boone, C., 2010. The genetic landscape of a cell. Science 327, 425-431. doi:10.1126/science.1180823.

Docherty, K. M., Charles F. Kulpa, J., 2005. Toxicity and antimicrobial activity of imidazolium and pyridinium ionic liquids. Green Chem. 7, 185-189. doi:10.1039/B419172B.

Eraso, P., Mazón, M. J., Portillo, F., 2006. Yeast protein kinase Ptk2 localizes at the plasma membrane and phosphorylates in vitro the C-terminal peptide of the H+-ATPase. Biochim. Biophys. Acta BBA—Biomembr. 1758, 164-170. doi:10.1016/j.bbamem.2006.01.010.

Erez, O., Kahana, C., 2002. Deletions of SKY1 or PTK2 in the *Saccharomyces cerevisiae* trk1Deltatrk2Delta mutant cells exert dual effect on ion homeostasis. Biochem. Biophys. Res. Commun. 295, 1142-1149.

Fung, S.-Y., Sofiyev, V., Schneiderman, J., Hirschfeld, A. F., Victor, R. E., Woods, K., Piotrowski, J. S., Deshpande, R., Li, S. C., de Voogd, N. J., Myers, C. L., Boone, C., Andersen, R. J., Turvey, S. E., 2013. Unbiased screening of marine sponge extracts for anti-inflammatory agents combined with chemical genomics identifies girolline as an inhibitor of protein synthesis. ACS Chem. Biol. doi: 10.1021/cb400740c.

Kaouass, M., Audette, M., Ramotar, D., Verma, S., De Montigny, D., Gamache, I., Torossian, K., Poulin, R., 1997. The STK2 gene, which encodes a putative Ser/Thr protein kinase, is required for high-affinity spermidine transport in *Saccharomyces cerevisiae*. Mol. Cell. Biol. 17, 2994-3004.

Keating, D. H., Zhang, Y., Ong, I. M., McIlwain, S., Morales, E. H., Grass, J. A., Tremaine, M., Bothfeld, W., Higbee, A., Ulbrich, A., Balloon, A. J., Westphall, M. S., Aldrich, J., Lipton, M. S., Kim, J., Moskvin, O. V., Bukhman, Y. V., Coon, J. J., Kiley, P. J., Bates, D. M., Landick, R., 2014. Aromatic inhibitors derived from ammonia-pretreated lignocellulose hinder bacterial ethanologenesis by activating regulatory circuits controlling inhibitor efflux and detoxification. Microb. Physiol. Metab. 5, 402. doi:10.3389/fmicb.2014.00402.

Kucharczyk, R., Dupre, S., Avaro, S., Haguenauer-Tsapis, R., Slonimski, P. P., Rytka, J., 2000. The novel protein Ccz1p required for vacuolar assembly in *Saccharomyces cerevisiae* functions in the same transport pathway as Ypt7p. J. Cell Sci. 113 Pt 23, 4301-4311.

Lee, C. M., Sedman, J., Neupert, W., Stuart, R. A., 1999. The DNA helicase, Hmi1p, is transported into mitochondria by a C-terminal cleavable targeting signal. J. Biol. Chem. 274, 20937-20942.

Li, C., Tanjore, D., He, W., Wong, J., Gardner, J. L., Sale, K. L., Simmons, B. A., Singh, S., 2013. Scale-up and evaluation of high solid ionic liquid pretreatment and enzymatic hydrolysis of switchgrass. Biotechnol. Biofuels 6, 1-14. doi:10.1186/1754-6834-6-154.

Li, Z., Ling, F., Shibata, T., 1998. Glucose repression on RIM1, a gene encoding a mitochondrial single-stranded DNA-binding protein, in *Saccharomyces cerevisiae*: a possible regulation at pre-mRNA splicing. Curr. Genet. 34, 351-359.

Luterbacher, J. S., Rand, J. M., Alonso, D. M., Han, J., Youngquist, J. T., Maravelias, C. T., Pfleger, B. F., Dumesic, J. A., 2014. Nonenzymatic Sugar Production from Biomass Using Biomass-Derived γ-Valerolactone. Science 343, 277-280. doi:10.1126/science.1246748.

Ouellet, M., Datta, S., Dibble, D. C., Tamrakar, P. R., Benke, P. I., Li, C., Singh, S., Sale, K. L., Adams, P. D., Keasling, J. D., Simmons, B. A., Holmes, B. M., Mukhopadhyay, A., 2011. Impact of ionic liquid pretreated plant biomass on *Saccharomyces cerevisiae* growth and biofuel production. Green Chem. 13, 2743. doi:10.1039/c1gc15327g.

Palmqvist, E., Hahn-Hägerdal, B., 2000. Fermentation of lignocellulosic hydrolysates. II: inhibitors and mechanisms of inhibition. Bioresour. Technol. 74, 25-33. doi:10.1016/S0960-8524(99)00161-3.

Parreiras, L. S., Breuer, R. J., Avanasi Narasimhan, R., Higbee, A. J., La Reau, A., Tremaine, M., Qin, L., Willis, L. B., Bice, B. D., Bonfert, B. L., Pinhancos, R. C., Balloon, A. J., Uppugundla, N., Liu, T., Li, C., Tanjore, D., Ong, I. M., Li, H., Pohlmann, E. L., Serate, J., Withers, S. T., Simmons, B. A., Hodge, D. B., Westphall, M. S., Coon, J. J., Dale, B. E., Balan, V., Keating, D. H., Zhang, Y., Landick, R., Gasch, A. P., Sato, T. K., 2014. Engineering and Two-Stage Evolution of a Lignocellulosic Hydrolysate-Tolerant *Saccharomyces cerevisiae* Strain for Anaerobic Fermentation of Xylose from AFEX Pretreated Corn Stover. PLoS ONE 9, e107499. doi:10.1371/journal.pone.0107499.

Parsons, A., Lopez, A., Givoni, I., Williams, D., Gray, C., Porter, J., Chua, G., Sopko, R., Brost, R., Ho, C., 2006. Exploring the mode-of-action of bioactive compounds by chemical-genetic profiling in yeast. Cell 126, 611-625. doi: 10.1016/j.cell.2006.06.040.

Piotrowski, J. S., Zhang, Y., Bates, D. M., Keating, D. H., Sato, T. K., Ong, I. M., Landick, R., 2014. Death by a thousand cuts: the challenges and diverse landscape of lignocellulosic hydrolysate inhibitors. Front. Microbiol. 5. doi:10.3389/fmicb.2014.00090.

Robinson, D. G., Chen, W., Storey, J. D., Gresham, D., 2014. Design and analysis of bar-seq experiments. G3 GenesGenomesGenetics 4, 11-18. doi:10.1534/g3.113.008565.

Robinson, M. D., McCarthy, D. J., Smyth, G. K., 2010. edgeR: a Bioconductor package for differential expression analysis of digital gene expression data. Bioinforma. Oxf. Engl. 26, 139-140. doi:10.1093/bioinformatics/btp616.

Sato, T. K., Liu, T., Parreiras, L. S., Williams, D. L., Wohlbach, D. J., Bice, B. D., Ong, I. S., Breuer, R. J., Qin, L., Busalacchi, D., Deshpande, S., Daum, C., Gasch, A. P., Hodge, D. B., 2013. Harnessing genetic diversity in *Saccharomyces cerevisiae* for improved fermentation of xylose in hydrolysates of alkaline hydrogen peroxide pretreated biomass. Appl. Environ. Microbiol. AEM.01885-13. doi: 10.1128/AEM.01885-13.

Schneider, R., Brors, B., Bürger, F., Camrath, S., Weiss, H., 1997. Two genes of the putative mitochondrial fatty acid synthase in the genome of *Saccharomyces cerevisiae*. Curr. Genet. 32, 384-388.

Smith, A. M., Heisler, L. E., Mellor, J., Kaper, F., Thompson, M. J., Chee, M., Roth, F. P., Giaever, G., Nislow, C., 2009. Quantitative phenotyping via deep barcode sequencing. Genome Res. 19, 1836-1842. doi:10.1101/gr.093955.109.

Socha, A. M., Parthasarathi, R., Shi, J., Pattathil, S., Whyte, D., Bergeron, M., George, A., Tran, K., Stavila, V., Venkatachalam, S., Hahn, M. G., Simmons, B. A., Singh, S., 2014. Efficient biomass pretreatment using ionic liquids derived from lignin and hemicellulose. Proc. Natl. Acad. Sci. 111, E3587-E3595. doi:10.1073/pnas.1405685111.

We claim:

1. A recombinant yeast of the species *Saccharomyces cerevisiae* that has been genetically engineered to:
   ferment xylose and exhibit a decreased level of functional protein tyrosine kinase 2 (PTK2) polypeptide,
   wherein the recombinant yeast has increased tolerance to ionic liquid toxicity and an improved growth rate in the presence of an ionic liquid relative to a wild-type yeast or another recombinant yeast not exhibiting a decreased level of functional PTK2;
   wherein the recombinant yeast comprises a deletion mutation or disrupting mutation of the *Saccharomyces cerevisiae* gene encoding PTK2.

2. The recombinant yeast of claim 1, wherein the ionic liquid is an imidazolium-based ionic liquid.

3. The recombinant yeast of claim 1, wherein the yeast comprises a deletion mutation in the *Saccharomyces cerevisiae* gene encoding PTK2.

4. The recombinant yeast of claim 1, wherein the yeast comprises a disrupting mutation in the *Saccharomyces cerevisiae* gene encoding PTK2.

5. The recombinant yeast of claim 1, wherein the yeast produces ethanol at an increased rate relative to a wild-type yeast or another recombinant yeast not exhibiting decreased or undetectable levels of functional PTK2 polypeptide.

6. The recombinant yeast of claim 5, wherein the increased rate of ethanol production occurs under anaerobic conditions.

7. A yeast inoculum, comprising: (a) a recombinant yeast of claim 1; and (b) a culture medium.

8. A method for fermenting cellulosic material into ethanol, comprising contacting an ionic liquid-treated hydrosylate of cellulosic material and the recombinant yeast of claim 1 or the yeast inoculum of claim 7 for a period of time sufficient to allow fermentation of at least a portion of the cellulosic material to ethanol, whereby more cellulosic material is fermented into ethanol in a hydrosylate comprising at least 1% residual ionic liquid than is fermented into ethanol in a hydrosylate comprising at least 1% residual ionic liquid that is not contacted to the recombinant yeast or the yeast inoculum.

9. The method of claim 8, wherein the ionic liquid-treated hydrosylate of cellulosic material comprises at least 1.5% residual ionic liquid.

10. The method of claim 8, wherein the ionic liquid-treated hydrosylate of cellulosic material comprises at least 2% residual ionic liquid.

11. The method of claim 8, further comprising separating the ethanol from fermented cellulosic material.

12. The method of claim 8, wherein the ionic liquid-treated hydrosylate of cellulosic material comprises xylose.

13. The method of claim 8, wherein the ionic liquid-treated hydrosylate of cellulosic material comprises lignocellulosic biomass.

14. The method of claim 13, wherein the lignocellulosic biomass comprises at least one material selected from the group consisting of agricultural residues, wood, municipal solid wastes, paper and pulp industry wastes, and herbaceous crops.

15. The method of claim 8, wherein the yeast comprises a deletion mutation in the *Saccharomyces cerevisiae* gene encoding PTK2.

16. The method of claim 8, wherein the yeast comprises a disrupting mutation m the *Saccharomyces cerevisiae* gene encoding PTK2.

17. A recombinant xylose fermenting *Saccharomyces cerevisiae* the comprises a deletion mutation or disrupting mutation of the *Saccharomyces cerevisiae* gene encoding wherein the recombinant xylose fermenting *Saccharomyces cerevisiae* exhibits a decreased level of functional PTK2 polypeptide and increased tolerance to ionic liquid toxicity relative to a wild-type *Saccharomyces cerevisiae* or another recombinant *Saccharomyces cerevisiae* not exhibiting a decreased level of functional PTK2.

* * * * *

UNITED STATES PATENT AND TRADEMARK OFFICE
CERTIFICATE OF CORRECTION

| | | |
|---|---|---|
| PATENT NO. | : 11,639,506 B2 | Page 1 of 1 |
| APPLICATION NO. | : 15/154537 | |
| DATED | : May 2, 2023 | |
| INVENTOR(S) | : Piotrowski et al. | |

It is certified that error appears in the above-identified patent and that said Letters Patent is hereby corrected as shown below:

On the Title Page

In Column 2, under "Other Publications", Line 35, delete "ciicuits" and insert --circuits-- therefor In the Claims In Column 31, Line 38, in Claim 7, after "comprising:", insert a linebreak In Column 31, Line 39, in Claim 7, after "and", insert a linebreak In Column 32, Line 36, in Claim 16, delete "m" and insert --in-- therefor In Column 32, Line 39, in Claim 17, delete "the" and insert --that-- therefor In Column 32, Line 40, in Claim 17, after "encoding", insert --PTK2,--

Signed and Sealed this
Seventh Day of January, 2025

Derrick Brent
*Acting Director of the United States Patent and Trademark Office*